(12) United States Patent
Arispe

(10) Patent No.: US 8,476,240 B2
(45) Date of Patent: Jul. 2, 2013

(54) HISTIDINE RELATED COMPOUNDS FOR IDENTIFYING AND BLOCKING AMYLOID BETA ION CHANNELS

(75) Inventor: Nelson Arispe, Silver Spring, MD (US)

(73) Assignee: The Henry M. Jackson Foundation for The Advancement of Military Medicine, Inc., Bethesda, MD (US)

( * ) Notice: Subject to any disclaimer, the term of this patent is extended or adjusted under 35 U.S.C. 154(b) by 208 days.

(21) Appl. No.: 12/933,029

(22) PCT Filed: Mar. 18, 2009

(86) PCT No.: PCT/US2009/037502
§ 371 (c)(1),
(2), (4) Date: Sep. 16, 2010

(87) PCT Pub. No.: WO2009/117480
PCT Pub. Date: Sep. 24, 2009

(65) Prior Publication Data
US 2011/0015139 A1 Jan. 20, 2011

Related U.S. Application Data

(60) Provisional application No. 61/037,857, filed on Mar. 19, 2008, provisional application No. 61/155,960, filed on Feb. 27, 2009.

(51) Int. Cl.
*A61K 38/06* (2006.01)
*A61K 38/07* (2006.01)
*A61K 38/05* (2006.01)
*A61K 31/00* (2006.01)
*C12P 13/04* (2006.01)
*A01N 61/00* (2006.01)

(52) U.S. Cl.
USPC ............. 514/21.9; 435/7.21; 435/106; 514/1; 514/21.91

(58) Field of Classification Search
None
See application file for complete search history.

(56) References Cited

U.S. PATENT DOCUMENTS

| | | | |
|---|---|---|---|
| 6,277,826 B1 | 8/2001 | Findeis et al. | |
| 8,324,278 B2 * | 12/2012 | Dioguardi | 514/561 |
| 2005/0171021 A1 * | 8/2005 | Cormier et al. | 514/17 |
| 2008/0214649 A1 * | 9/2008 | Yu et al. | 514/423 |

FOREIGN PATENT DOCUMENTS

| | | |
|---|---|---|
| WO | WO03/091689 | * 11/2003 |
| WO | 2007115372 | 10/2007 |

OTHER PUBLICATIONS

Thermo. Technical Information N-Terminal Acetylation and C-Termini Amidation of Peptides. 2004, 2 pages.*
Oehlke et al. Enhanced Incorporation of Nonhydrolyzable Tritium in Gnrh and Trf by Catalytic Exchange Labeling. Journal of Labelled Compounds and Radiopharmaceuticals. 1987, vol. XXIV, No. 12, pp. 1483-1491.*
Vallat, Philippe et al., "Structure-Lipophilicity and Structure-Polarity Relationships of Amino Acids and Peptides," Helvetica Chimica Acta, 1995, vol. 78, No. 2, pp. 471-485; XP002624197.
"Oligohistidine target peptide sequence SeqID 1," Mar. 11, 2004, p. 1; XP002624196; retrieved from EBI accession No. GSP:ADH22656.
Yokoyama, Keiichi et al., "Peptide Inhibitors for Angiotensin I-Converting Enzyme from Thermolysin Digest of Dried Bonito," Biosci. Biotech. Biochem., 56 (10), 1992, pp. 1541-1545.
Tujebajeva, Rosa M. et al., "Selenoprotein P Expression, Purification and Immunochemical Characterization," The Journal of Biological Chemistry, vol. 275, No. 9, Mar. 3, 2000, pp. 6288-6294.
Knecht, Steven et al., "Oligohis-tags: mechanisms of binding to Ni2+-NTA surfaces," J. Mol. Recognit., 2009, 22, pp. 270-279.
Arispe, Nelson et al., "Efficiency of Histidine-Associating Compounds for Blocking the Alzheimer's Aβ Channel Activity and Cytotoxicity," Biophysical Journal, vol. 95, Nov. 2008, pp. 4879-4889.
Diaz, Juan Carlos et al., "Histidines 13 and 14 in the Aβ sequence are targets for inhibition of Alzheimer's disease Aβ ion channel and cytotoxicity," Biol. Res., 39, 2006, pp. 447-460.
Arispe, N., "Architecture of the Alzheimer's Aβ P Ion Channel Pore," The Journal of Membrane Biology, vol. 197, No. 1, 2004, pp. 33-48.
Simakova, Olga et al., "Early and Late Cytotoxic Effects of External Application of the Alzheimer's Aβ Result from the Initial Formation and Function of Aβ Ion Channels," Biochemistry, 2006, 45, pp. 5907-5915.
Arispe, Nelson et al., "Aβ ion channels. Prospects for treating Alzheimer's disease with Aβ channel blockers," Biochimica et Biophysica Acta, 2007, pp. 1-14.

* cited by examiner

*Primary Examiner* — Marcela M Cordero Garcia
(74) *Attorney, Agent, or Firm* — MH2 Technology Law Group, LLP

(57) ABSTRACT

The present disclosure relates to amyloid beta (Aβ) channels and the diseases and disorders caused by abnormal activity in these channels, such as Alzheimer's disease, Lewy body dementia, inclusion body myositis, or cerebral amyloid angiopathy. The disclosure provides compositions and methods that block Aβ channel activity and/or reduce Aβ-induced toxicity in a cell. Compositions comprised of compounds having histidine coordinating capacity are used in methods to prevent, reduce, or eliminate damage caused by Aβ ion channels.

4 Claims, 21 Drawing Sheets

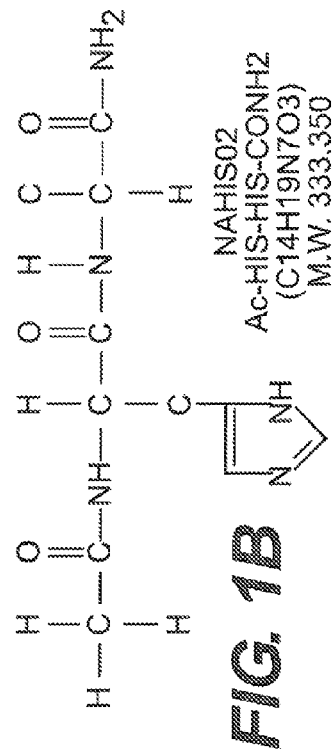
FIG. 1A
NAHIS01
Ac-HIS-CONH2
(C8H12N4O2)
M.W.: 196.209
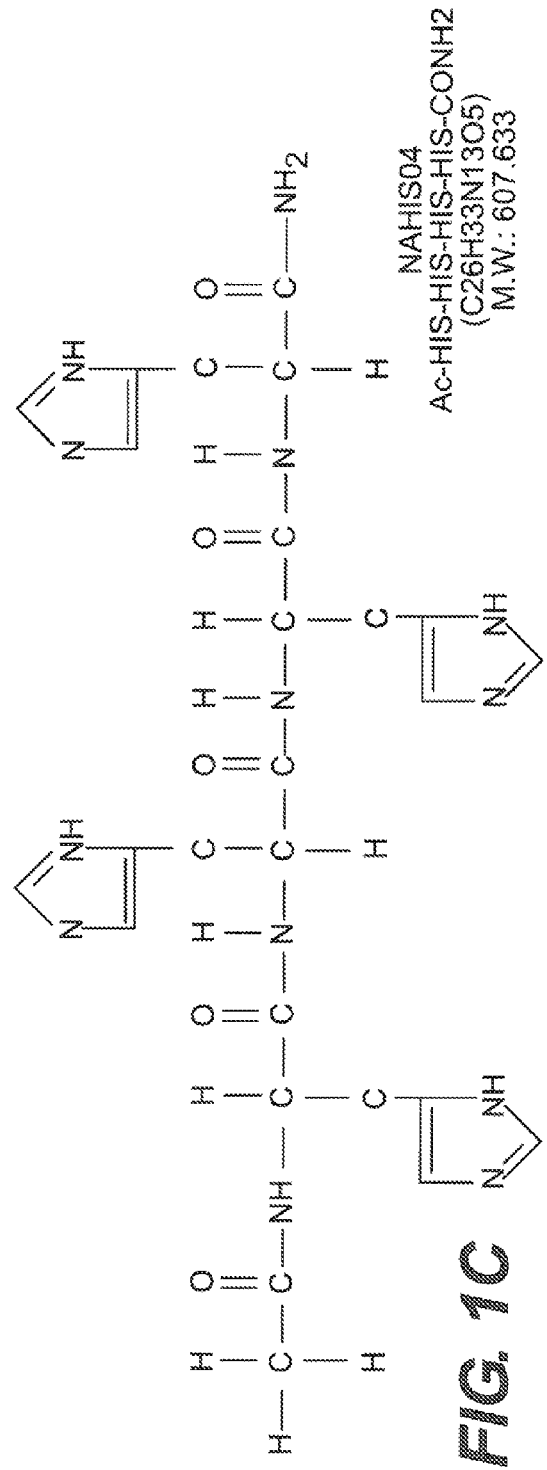
FIG. 1B
NAHIS02
Ac-HIS-HIS-CONH2
(C14H19N7O3)
M.W.: 333.350
FIG. 1C
NAHIS04
Ac-HIS-HIS-HIS-HIS-CONH2
(C26H33N13O5)
M.W.: 607.633
(SEQ ID NO: 2)
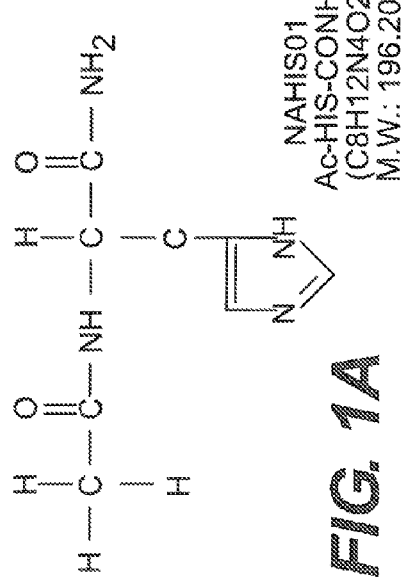

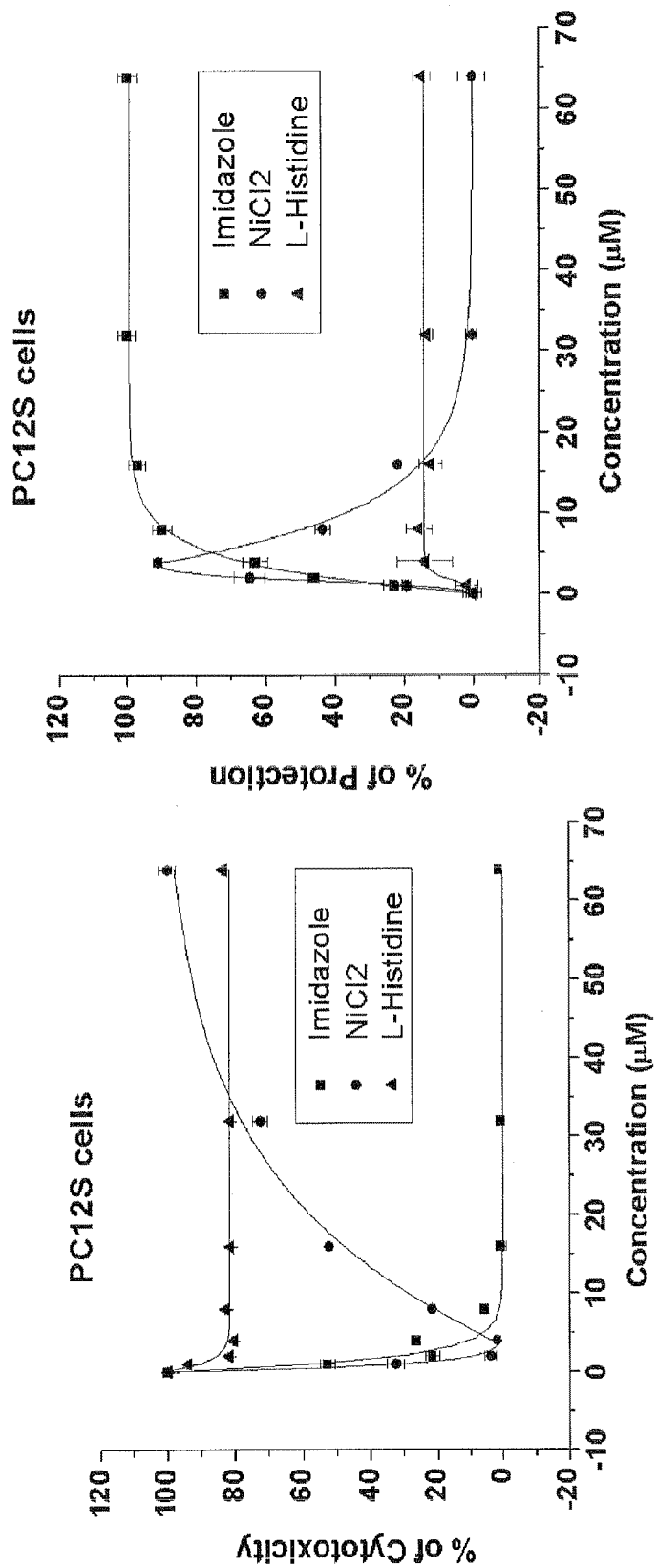

| | EC50 | Hill slope |
|---|---|---|
| NA4 | 1.24878 ±0.66295 | 0.57092 ±0.14312 |
| NA7 | 1.10508 ±0.48604 | 0.84816 ±0.25854 |
| ARISPHIS04 | 0.42319 ±0.00707 | 4.34964 ±0.24096 |

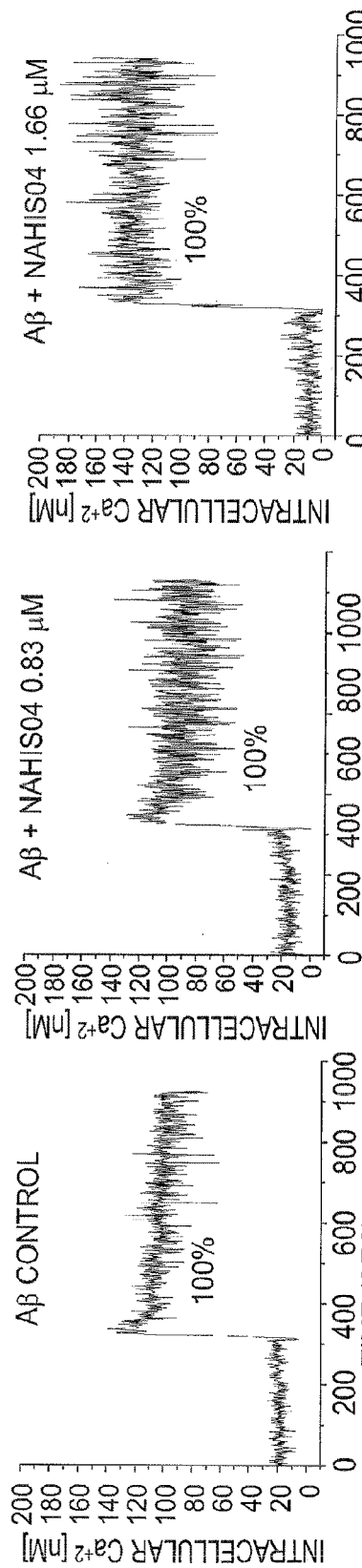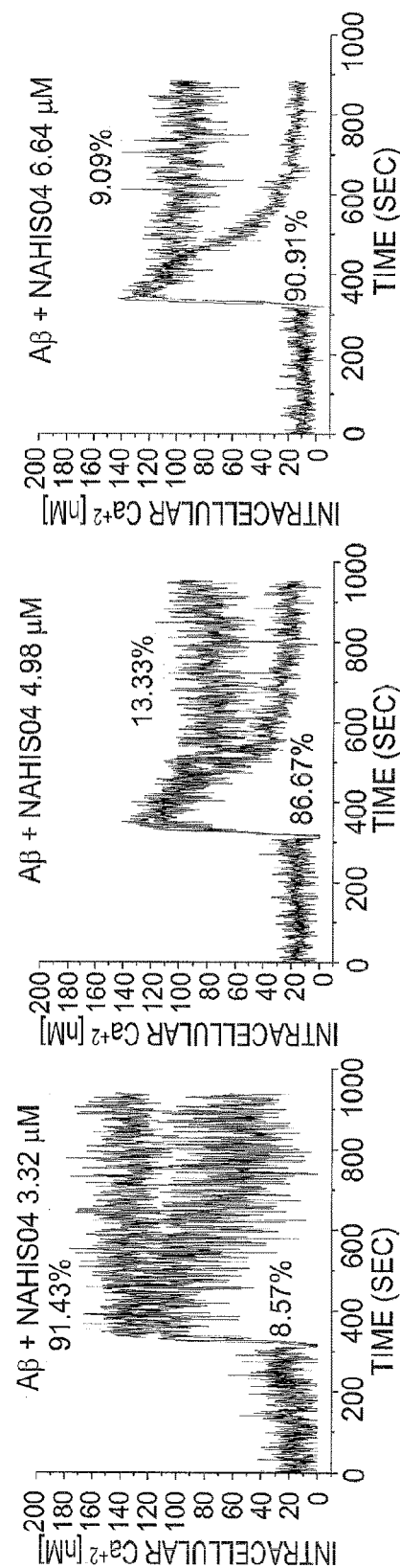

SEQUENCE LISTING

<160> NUMBER OF SEQ ID NOS: 5

<210> SEQ ID NO 1
<211> LENGTH: 42
<212> TYPE: PRT
<213> ORGANISM: Homo sapiens

<400> SEQUENCE: 1

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 2

His His His His
1

<210> SEQ ID NO 3
<211> LENGTH: 7
<212> TYPE: PRT
<213> ORGANISM: Homo sapiens

<400> SEQUENCE: 3

Ser Gly Tyr Glu Val His His
1               5

<210> SEQ ID NO 4
<211> LENGTH: 7
<212> TYPE: PRT
<213> ORGANISM: Homo sapiens

<400> SEQUENCE: 4

Glu Val His His Gln Lys Leu
1               5

<210> SEQ ID NO 5
<211> LENGTH: 7
<212> TYPE: PRT
<213> ORGANISM: Homo sapiens
<220> FEATURE:
<223> OTHER INFORMATION: N-term acetylated
<220> FEATURE:
<223> OTHER INFORMATION: C-term amidated

<400> SEQUENCE: 5

Ser Gly Tyr Glu Val His His
1               5
```

HISTIDINE RELATED COMPOUNDS FOR IDENTIFYING AND BLOCKING AMYLOID BETA ION CHANNELS

CROSS-REFERENCE TO RELATED APPLICATIONS

This is the U.S. National Phase application of International Application PCT/US2009/037502, which claims the benefit of, and relies on the filing date of, U.S. provisional patent application No. 61/037,857, filed 19 Mar. 2008, and U.S. provisional application No. 61/155,960, filed 27 Feb. 2009, the entire disclosures of which are hereby incorporated herein by reference.

STATEMENT OF GOVERNMENT INTEREST

This invention was made partially with U.S. Government support from The Uniformed Services for the Health Sciences. The U.S. Government has certain rights in the invention.

BACKGROUND

Amyloid plaques, which appear to be mainly composed of beta amyloid peptides (Aβ), are found in Alzheimer's disease, some variants of Lewy body dementia, and inclusion body myositis. Aβ aggregates are also found to coat cerebral blood vessels in cerebral amyloid angiopathy. The Aβ peptide is derived by proteolysis of a larger membrane-bound β-amyloid precursor peptide (Haass and Selkoe, 1993).

The most well known disease involving amyloid plaques is Alzheimer's disease (AD), an irreversible, progressive brain disease that slowly destroys memory and thinking skills. AD is the most common cause of dementia among older people, but it is not a normal part of aging. AD starts in a region of the brain that affects recent memory and then gradually spreads to other parts of the brain. Damage to the brain may begin as many as 10-20 years before any obvious signs of forgetfulness appear. As nerve cells die throughout the brain, affected regions begin to shrink. By the final stage of AD, damage to the brain is widespread. According to the U.S. National Institute on Aging, 2.4 to 4.5 million Americans currently have AD. Projections using current population trends suggest that the number of Americans with AD will increase significantly. This increase of AD patients will not only affect their families, but will also put a heavy economic burden on society unless more effective treatments can be found.

Although a consensus on the primary mechanisms that cause neuronal damage in AD remains elusive, numerous reports have associated the cytotoxicity of Aβ peptides with the neurodegeneration observed in specific brain areas of AD patients (Yankner, 1996; Yankner, 2000; Hardy and Higgens, 1992, Hardy and Selkoe, 2002). It has been shown that addition of fresh aggregates of Aβ to cell cultures generates a potentially toxic increase in the intracellular calcium concentration (Mattson et al., 1992; Kawahara et al., 2000; Zhu et al., 2000; Demuro et al., 2005; Simakova and Arispe, 2006). Years of research support the concept that disturbances of intracellular calcium homeostasis may play a pathological role in the neurodegeneration associated with AD (Mattson et al., 1993; Kawahara, 2004; LaFerla, 2002; Smith et al., 2005).

A mechanism for the Aβ peptide-induced increase in intracellular calcium was originally proposed based on the formation of an independent tromethamine and aluminum-sensitive Aβ channel (Arispe et al., 1993). This Aβ channel, which permits the entrance of extracellular calcium ions into the cell (Arispe et al., 1994; Aripse et al., 2007), has been confirmed in a variety of membranes by many researchers over the past decade (Kawahara et al., 1997; Rhee et al., 1998; Lin et al., 1999; Kourie et al., 2001; Kagan et al., 2002), has been observed with atomic force microscopy (Quist et al., 2005; Lal et al., 2007), and has been subjected to theoretical modeling (Durrell et al., 1994; Jang et al., 2007; Jang et al., 2008). The asymmetry in one of the models (Durrell et al., 1994) explains the finding that zinc preferentially binds and blocks only one side of the Aβ channel (Arispe et al., 1996). It has been frequently demonstrated in studies of different metalloproteases, as well as in the Aβ molecule, that sites rich in Histidine (His) and anionic residues are associated with $Zn^{2+}$ binding (Chakrabarti, 1990; Perlman and Rosner, 1994; Becker and Roth, 1993; Miura et al., 2000; Yang et al., 2000). Because of the unique chemical nature of the His residue, it has a strong metal affinity. His residues act as a ligand to a metal center (Mukherjee and Bagchi, 2006) bridging imidazole groups from the side chains of His residues (Yang et al., 2000). In the theoretical models of Durell et al. (1994), the least energy calculations for the full size Aβ channels, imbedded in a lipid environment, position the rings of $His_{13}$ and $His_{14}$ of the Aβ molecule around the entrance of the putative pore. To test this prediction for the modeling algorithm, it has recently been shown that peptide fragments of Aβ containing the two neighboring $His_{13}$ and $His_{14}$ residues effectively block Aβ channel activity in planar lipid bilayers (Arispe et al., 2007; Aripse, 2004; Diaz et al., 2006). When the His-His diad is substituted with residues lacking a propensity to interact with His residues, the Aβ-derived peptides lose their effectiveness to both block the Aβ channel and to prevent Aβ peptide cytotoxicity (Diaz et al., 2006). Furthermore, methylation of the imidazole side chains of His residues in the Aβ-derived peptide prevents the formation of His bridges, and also results in abolition of Aβ peptide neurotoxicity (Tickler et al., 2005).

Although progress has been made in evaluating Aβ-derived peptides that can block the Aβ channel and prevent Aβ peptide cytotoxicity, these peptides represent fragments of the Aβ polypeptide and thus present potential limitations as therapeutic molecules, including possible interactions with other natural molecules, such as the β-amyloid precursor protein, and resistance to crossing certain natural barriers, such as the blood brain barrier.

SUMMARY

The present disclosure provides compositions and methods for treating or preventing diseases that involve Aβ ion channels, such as AD. As a general matter, the compositions and methods extend the life of a living cell by affecting the Aβ channels in the cell membrane. The compositions and methods may prevent the formation of Aβ channels or may affect the functionality of Aβ channels. As disclosed herein, compounds with a histidine coordinating capacity, such as $Ni^{2+}$, imidazole, histidine and histidine-related compounds, interfere with the currents and cytotoxicity of Aβ channels. Previous studies have shown that polypeptide fragments of the Aβ molecule have the ability to interfere with the currents and cytotoxicity of Aβ channels. The present disclosure, however, provides compositions comprising compounds with a histidine coordinating capacity, other than polypeptide fragments of the Aβ molecule, and, therefore, makes available a large pool of compositions that can be used to treat diseases or disorders involving Aβ channels.

Broadly speaking, the present disclosure provides compositions and methods of treating at least one cell with at least one compound having a histidine coordinating capacity, thereby preventing, reducing, or eliminating damage caused by Aβ channels. The compositions and methods can be practiced in vivo as either therapy for treating a disease or disorder involving Aβ channels or as a prophylactic method to prevent the formation and/or operation of Aβ channels. Likewise, the method can be practiced in vitro to detect the effects of Aβ channels on cells or to detect the effects of combining compounds with histidine coordinating capacity with other compounds or drugs on cells.

In a first aspect, the present disclosure provides compositions comprising a compound having a histidine coordinating capacity that cause a change in the flow of current through an Aβ channel. In certain embodiments, a composition comprises a sufficient amount of at least one compound having a histidine coordinating capacity to cause a detectable change in the flow of current through an Aβ channel. Thus, when used in methods of treating, the compositions comprise at least one compound having a histidine coordinating capacity in an amount effective to cause a detectable change in the flow of current in at least one Aβ channel in a cell of a subject.

In a second aspect, the present disclosure provides compositions comprising a compound having a histidine coordinating capacity that reduce the Aβ-induced toxicity in a cell. In certain embodiments, a composition comprises a sufficient amount of at least one compound having a histidine coordinating capacity to cause a detectable reduction in the Aβ-induced toxicity in a cell. This aspect can be used in methods of treating, whereby the compositions comprise at least one compound having a histidine coordinating capacity in an amount effective to reduce the Aβ-induced toxicity in a cell of a subject. Also contemplated is a composition comprising a compound having a histidine coordinating capacity for use in therapy.

In a third aspect, the present disclosure provides compositions comprising a compound having a histidine coordinating capacity that prevent the formation of Aβ channels. This aspect can be used in methods of preventing a disease, whereby the compositions comprise at least one compound having a histidine coordinating capacity in an amount effective to prevent the formation of at least one Aβ channel in a cell of a subject.

In embodiments, the substances are provided in an amount sufficient to provide one or more doses to a subject. Certain other aspects provide for use in the preparation of compositions for medical use, such as pharmaceutical or therapeutic compositions. Compositions may comprise a compound having a histidine coordinating capacity that affects Aβ activity along with one or more other substances, which are typically substances that are biologically tolerable in that they may be exposed to living cells at their useful concentrations without killing the cells. In embodiments, the other substances are pharmaceutically acceptable substances.

In another aspect, a container is provided, wherein the container comprises one or more compounds having a histidine coordinating capacity that cause a change, such as a decrease, in the flow of current through an Aβ channel and/or in the Aβ-induced toxicity in a cell. The compound having a histidine coordinating capacity may also prevent the formation of at least one Aβ channel. In general, where designed for in vivo treatment of a subject, the container contains a sufficient amount of the compound having a histidine coordinating capacity to provide at least one dose to the subject. In some embodiments, kits comprising one or more containers are provided.

The present disclosure also provides methods of treating individuals that are suffering from or may be susceptible to a disease or disorder involving Aβ channels. In certain embodiments, the methods comprise administering to an individual (used interchangeably herein with "subject" and "patient") an amount of a composition comprising a compound having histidine coordinating capacity sufficient to reduce, eliminate, or prevent cell, tissue, or organ damage in the individual that is caused by Aβ channel activity. In one embodiment, the disease is Alzheimer's disease. In another embodiment, the disease or disorder is Lewy body dementia, inclusion body myositis, or cerebral amyloid angiopathy. Also contemplated is a composition comprising a compound having a histidine coordinating capacity, as described herein, for use in treatment of Alzheimer's disease, Lewy body dementia, inclusion body myositis, or cerebral amyloid angiopathy.

In a further aspect, the disclosure provides methods to reduce Aβ-induced toxicity in a cell. This may involve administering to a cell that has been exposed to the Aβ protein an amount of a composition comprising a compound having a histidine coordinating capacity that is sufficient to reduce Aβ-induced toxicity in the cell.

In still another aspect, methods are provided to change the flow of current through an Aβ channel in a cell, such as in the plasma membrane of the cell. This method may comprise administering to the cell an amount of the composition comprising a compound having a histidine coordinating capacity sufficient to reduce the flow of current through the Aβ channel in the plasma membrane of the cell.

In a different aspect, methods to prevent formation of Aβ channels are provided. The method may comprise administering to the cell an amount of the composition comprising a compound having a histidine coordinating capacity sufficient to prevent the complete formation of at least one Aβ channel. This method may be used to prevent certain diseases or disorders that are characterized by the presence of Aβ channels.

In a final aspect, the disclosure provides methods to identify Aβ channels. This method may comprise administering to the cell an amount of the composition comprising a compound having a histidine coordinating capacity sufficient to detect the presence of at least one Aβ channel. This method may be used to identify certain diseases or disorders that are characterized by the presence of Aβ channels.

BRIEF DESCRIPTION OF THE DRAWINGS

The accompanying drawings, which constitute a part of this specification, illustrate several embodiments of the invention and, together with the written description, serve to explain various principles of the invention.

FIG. 1 depicts the chemical structures of the histidine-related compounds NAHIS01, NAHIS02, and NAHIS04, each of which is amidated at the carboxy terminus and acetylated at the amino terminus. NAHIS01, NAHIS02, and NAHIS04 are referred to as ARISPHIS01, ARISPHIS02, and ARISPHIS04, respectively, in U.S. Provisional Application No. 61/037,857.

FIG. 11 depicts intracellular free calcium change in PC12 cells before (Panel A) and after the addition of Aβ peptide to media containing different concentrations of NAHIS04 (Panel B: 0.83 µM; Panel C: 1.66 µM; Panel D: 3.32 µM; Panel E: 4.98 µM; Panel F: 6.64 µM).

DETAILED DESCRIPTION

Figures 2A, 2B:
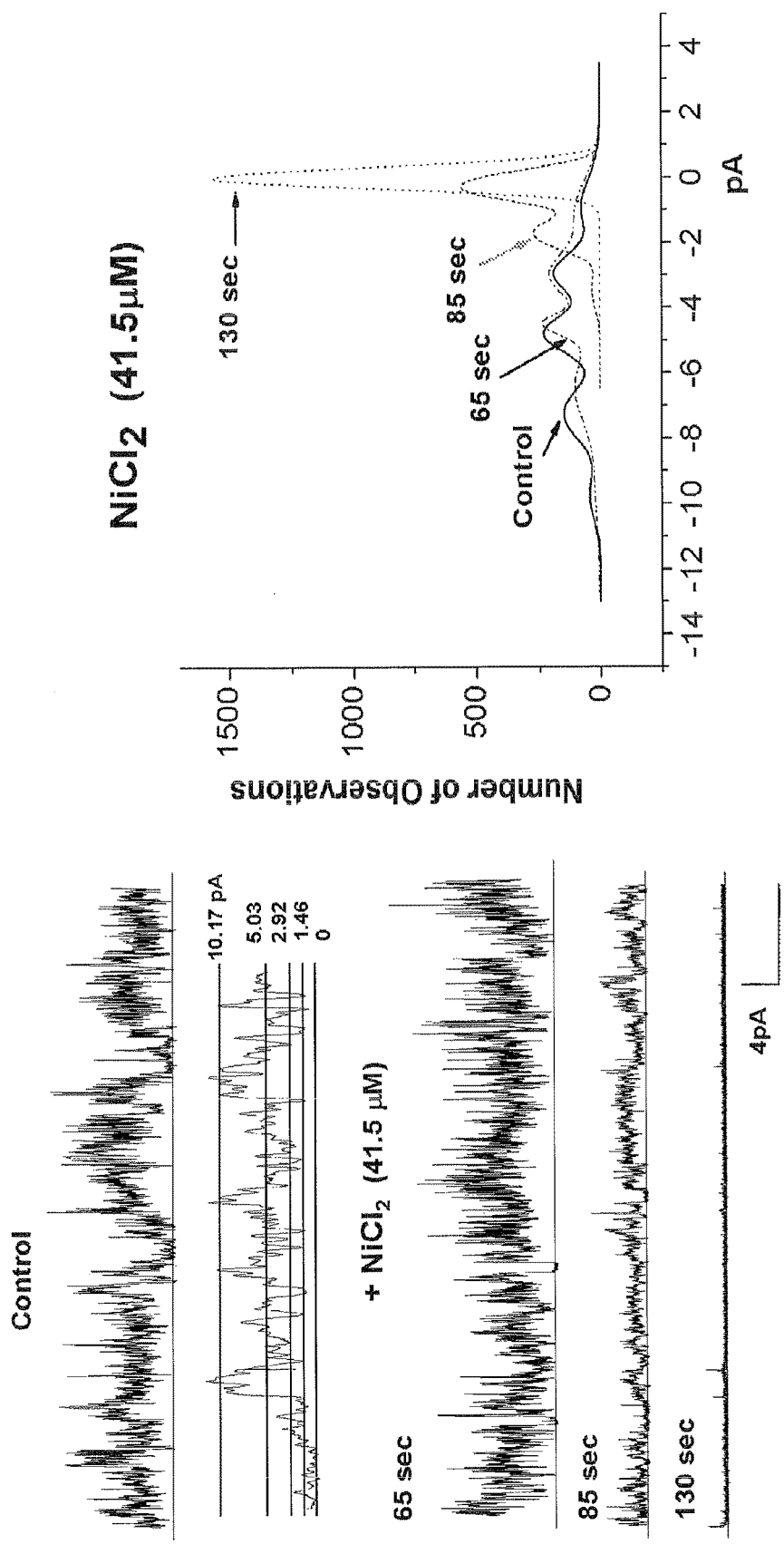
FIG. 2 illustrates that nickel and imidazole irreversibly block the membrane-bound Aβ ion channel. (A and C) Electrical activity across a lipid bilayer with incorporated Aβ channels, recorded before (control) and in the presence of either $Ni^{2+}$ (A) or imidazole (C). The membrane electrical potential in the experiment was maintained at zero level. B and D display the current amplitude histograms of the channel activity from the current traces in A and C. Five main current peaks of 0.8, 3.2, 5.2, 7.5, and 10 pA characterize the Aβ channel activity. Both compounds quickly abolish the most frequent current peaks.

Reference will now be made in detail to various exemplary embodiments, examples of which are illustrated in the accompanying drawings. The following detailed description is provided to give details on certain embodiments, and should not be understood as a limitation on the full scope of the invention.

Broadly speaking, the present disclosure provides methods, compounds, and compositions for reducing Aβ-induced toxicity of a cell, changing the flow of current through an Aβ protein channel, and/or preventing the formation of Aβ protein channels. The methods, compounds, and compositions disclosed herein also have use in preventing diseases or disorders caused by Aβ-induced toxicity of a cell, such as AD. They thus have both in vivo and in vitro uses.

The Aβ peptide or protein discussed herein interacts with cells, such as neurons, to generate an increase in intracellular calcium concentrations. The Aβ channel, Aβ ion channel, or Aβ protein channel refers to an independent channel that is formed by oligomeric aggregates of the Aβ peptide (SEQ ID NO:1) and that conducts calcium into the cell. The channel is usually found in the lipid bilayer of a plasma membrane of a cell. The compositions and methods disclosed herein can be used for detecting the presence of, the development of, or the possible development of, a disease or disorder by detecting the presence of Aβ channels, aggregates of Aβ protein, amyloid plaques, or other structures comprised of Aβ protein.

In view of the breadth of cells, diseases, and disorders encompassed by the present invention, it should be recognized that all cells in which an Aβ protein channel is found are contemplated. Likewise, all diseases and disorders in which an Aβ channel may be found to be involved are contemplated. For example, the disease or disorder may be, but is not limited to, Alzheimer's disease, some variants of Lewy body dementia, inclusion body myositis, and cerebral amyloid angiopathy. Accordingly, in one aspect, the disclosure provides a method of detecting the presence of, the development of, or the possible development of, a disease or disorder by detecting the presence of Aβ channels in a cell or amyloid plaques or fibrils in tissue.

Therefore, the disclosure provides compositions comprising compounds having a histidine coordinating capacity, such as $Ni^{2+}$, imidazole, histidine and histidine-related compounds, that can be used to treat a disease or disorder. The term "histidine coordinating capacity" refers to the ability of a compound to interact with the histidine residues of the Aβ channel and can be measured using assays known in the art and/or disclosed in the examples of this application, including, for example, the ability to reduce Aβ-mediated channel activity, such as current, calcium influx, and cytotoxicity. Compounds with histidine coordinating capacity include histidines with reactive imidazole side chains. Imidazole has a resonance structure that makes it an excellent nucleofile. Therefore, imidazole has a propensity to interact with other charged residues, especially His residues. In certain embodiments, the compounds having a histidine coordinating capacity are isolated.

In one embodiment, the composition comprises a polypeptide having at least 2 but no more than 10 amino acid residues, wherein at least 2 but no more than 4 of those amino acid residues are histidine, wherein the polypeptide is not a fragment of the Aβ protein, and wherein the Aβ protein has the amino acid sequence of SEQ ID NO:1. In certain embodiments, the polypeptide has no more than 6, 7, 8, or 9 amino acid residues, no more than 4 histidine residues, and/or no more than 2 histidine residues. In other embodiments, the polypeptide consists of 4 histidine residues or consists of 2 histidine residues. For purposes of the present invention, the terms protein, polypeptide and peptide are used interchangeably. In certain embodiments, the polypeptide is isolated. As used herein, "isolated," when used to describe the various compounds or polypeptides, means a compound or polypeptide that has been separated and/or recovered from one or more components of its natural environment.

Modifications of the polypeptide or peptide are envisioned that make it more amenable for in vivo use. For example, the polypeptide or peptide may be chemically modified using methods known in the art. These modifications may result in less proteolytic degradation, an increase in bioavailability, better permeability across the blood-brain barrier, etc. As an example, chemical modification of the polypeptide, such as methylation of the amide bond nitrogen, may improve stability of the polypeptide. As another example, the ends of the histidine residue(s) may be end-capped to avoid interactions of the ends with other reactive groups found in the Aβ channel. For example, the amino terminus of the polypeptide or peptide may be acetylated and the carboxy terminus of the polypeptide or peptide may be amidated. The peptides can also be end-capped by methylation, biotinylation or by using other protecting groups, such as 9H-(f)luoren-9-yl(m)eth(o)xy(c)arbonyl (Fmoc). These modifications can also be made to polypeptide fragments of Aβ to improve the ability of the fragments to block the Aβ channel and/or reduce the concentration required to block the Aβ channel.

Certain other aspects of the invention provide for use in the preparation of compositions for medical use, such as pharmaceutical or therapeutic compositions. Compositions may comprise compounds having a histidine coordinating capacity, such as the polypeptides described herein, along with one or more other substances, which are typically substances that are biologically tolerable in that they may be exposed to living cells without killing the cells. In embodiments, the compositions can comprise cells, tissues, proteins, nucleic acids, or other small or complex molecules typically found in biological samples. Compositions may also comprise some or all of the reagents, compounds, labels, etc. that are used in one or more of the various assays mentioned herein. In embodiments, the compositions comprise one or more substances that are pharmaceutically acceptable. As used herein, a "pharmaceutically acceptable substance" is one that is not toxic to a cell to which it is contacted, at the concentration at which it is contacted with the cell. The pharmaceutically acceptable substance thus may be toxic at the level present in the composition, but upon administration to a subject, is diluted to a safe level. The term is thus intended to include, but not be limited to, solvents, coatings, antibacterial and antifungal agents, and any other ingredient that is biologically tolerable. Examples of such substances include, but are not limited to, water, saline, human serum albumin, sugars, salts, lipids, drugs, carriers, flavorants, fillers, binders, gums, colorants, buffers, detergents, biologically active compounds, and the like. In a preferred embodiment, the compositions comprise pharmaceutical carriers that are useful in preparing pharmaceutical formulations, such as surfactants, polyethylene glycol, fatty acids, liposomes, solutes that render the substance isotonic with the blood, and the like. The use of such pharmaceutically active substances is well known in the art. Preferably, and particularly for compositions intended for in vivo use, the composition is sterile or has been sterilized. Sterilization may be performed by any suitable technique. In one embodiment, the composition is a freeze dried (lyophilized) composition requiring only the addition of a sterile liquid carrier, for example, water for injections, immediately prior to use.

The compositions disclosed herein can cause a detectable change in the flow of current through an Aβ channel and/or reduce the Aβ-induced toxicity in a cell. Assays that measure electrical conductances can be employed to determine the flow of current and assays to measure cell death can be employed to measure reduction of Aβ-induced toxicity. An example of an in vitro assay to measure changes in electrical current is described in the Examples below. Examples of assays to measure cell death include a colorimetric assay and a lactate dehydrogenase assay, as described herein. Assays to determine the presence of Aβ ion channels and/or amyloid plaques or fibrils include Aβ immunoreactivity, light-scattering spectroscopy, circular dichroism spectroscopy, electron microscopy, and examination of brain tissue, for example. Other assays, whether for in vitro or in vivo use, are well known in the art.

Another aspect provides a container comprising one or more compounds having a histidine coordinating capacity, such as the polypeptides described herein, that cause a change in the flow of current through an Aβ channel and/or reduce the Aβ-induced toxicity in a cell. The container may also comprise one or more compounds having a histidine coordinating capacity, such as the polypeptides described herein, that prevent the formation of Aβ channels. In general, where designed for in vivo treatment of a subject, a container according to the invention contains a sufficient amount of substance to provide at least one dose to the subject. Where designed for in vitro use, a container typically contains at least enough of at least one substance to conduct an assay according to the invention. In certain embodiments, the container is provided in a package with one or more other containers and/or with one or more articles of manufacture or devices having use in delivery of substances to subjects (e.g., syringes, needles, antiseptic swabs), or for practice of the methods of the invention in vitro.

The present disclosure also provides kits. In general, the kits comprise a sufficient amount of at least one compound having a histidine coordinating capacity, such as the polypeptides described herein, to cause a change in the flow of current through an Aβ channel and/or reduce the Aβ-induced toxicity in a cell. The kits may also comprise one or more compounds having a histidine coordinating capacity, such as the polypeptides described herein, that prevent the formation of Aβ channels. Typically, the compound will be supplied in one or more container, each container containing a sufficient amount of the compound for at least one dosing of the patient. The kits can comprise other components, such as some or all of the components necessary to practice a method of the invention. The kits may contain a syringe for administering a dose of the substance. The kits may also comprise filters for sterilization prior to delivery. They may likewise contain sterile water or buffer for rehydration or reconstitution of dry substance, prior to administration to a patient. In embodiments, multiple doses of the compound are provided in the kit, either all in a single container (e.g., a vial) or distributed among two or more containers. Preferably, the kit and its contents are sterile or have been sterilized.

In general, a dosing of about 0.01 ng to about 1 g, such as about 0.05 ng, 0.1 ng, 0.5 ng, 1 ng, 10 ng, 50 ng, 100 ng, 500 ng, 1 μg, 5 μg, 10 μg, 50 μg, 100 μg, 500 μg, or 1 g per administration should be effective in providing the desired therapeutic or prophylactic result. Of course, injection or infusion amounts will tend to be on the lower end of the range while oral administration amounts will tend to be on the upper end. In vitro results suggest that μM amounts are optimal but of course these amounts will vary depending on the species of the subject and the reason for administration.

The present disclosure also provides methods of using the compositions described herein. In one aspect, a method of reducing Aβ-induced toxicity in a cell is provided, the method comprising administering to a cell that has been exposed to the Aβ protein an amount of a composition disclosed herein sufficient to reduce Aβ-induced toxicity in the cell. In one embodiment, the composition comprises a polypeptide having at least 2 but no more than 6-10 amino acid residues, wherein at least 2 but no more than 4 of those amino acid residues are histidine, wherein the polypeptide is not a fragment of the Aβ protein, and wherein the Aβ protein has the amino acid sequence of SEQ ID NO:1. In another embodiment, the composition comprises a polypeptide consisting of four histidine residues. In yet another embodiment, the composition comprises a peptide consisting of two histidine residues. By reduction in Aβ-induced toxicity in a cell, it is meant that the compositions protect the cell from damage or further damage caused by Aβ channels, usually in the plasma membrane of the cell.

In another aspect, a method for reducing the flow of current through an Aβ channel in the plasma membrane of a cell is provided, the method comprising administering to the cell an amount of a composition disclosed herein sufficient to reduce the flow of current through the Aβ channel in the plasma membrane of the cell. In one embodiment, the composition comprises a polypeptide having at least 2 but no more than 6-10 amino acid residues, wherein at least 2 but no more than 4 of those amino acid residues are histidine, wherein the polypeptide is not a fragment of the Aβ protein, and wherein the Aβ protein has the amino acid sequence of SEQ ID NO:1. In another embodiment, the composition comprises a polypeptide consisting of four histidine residues. In yet another embodiment, the composition comprises a peptide consisting of two histidine residues.

In still another aspect, the compositions disclosed herein can be used in methods of treating individuals that are suffering from or may be susceptible to a disease or disorder involving Aβ channels. In general, such methods comprise administering to an individual an amount of a composition having histidine coordinating capacity sufficient to reduce, eliminate, or prevent cell, tissue, or organ damage that is caused by Aβ channel activity. More specifically, the disclosure provides a method of treating a subject suffering from a disease or disorder associated with Aβ channel formation, comprising administering to the subject an amount of a composition disclosed herein sufficient to reduce Aβ-induced toxicity in the subject. In one embodiment, the composition comprises a polypeptide having at least 2 but no more than 6-10 amino acid residues, wherein at least 2 but no more than 4 of those amino acid residues are histidine, wherein the polypeptide is not a fragment of the Aβ protein, and wherein the Aβ protein has the amino acid sequence of SEQ ID NO:1. In another embodiment, the composition comprises a polypeptide consisting of four histidine residues. In yet another embodiment, the composition comprises a peptide consisting of two histidine residues. Also contemplated are these compositions for use in therapy, generally, as well as, more specifically, these compositions for use in the treatment of Alzheimer's disease, Lewy body dementia, inclusion body myositis, or cerebral amyloid angiopathy.

Administering or contacting means any action that results in at least one compound in the composition physically contacting at least one cell. It thus may comprise exposing the cell(s) to compositions of the invention in an amount sufficient to result in contact of at least one compound with histidine coordinating capacity with at least one cell. The methods can be practiced in vivo, in which case contacting means exposing at least one cell in a subject to at least one compound in a composition of the invention. In general, the amount of composition of the invention to contact the cell is about 0.01 ng to about 1 g, such as about 0.05 ng, 0.1 ng, 0.5 ng, 1 ng, 10 ng, 50 ng, 100 ng, 500 ng, 1 μg, 5 μg, 10 μg, 50 μg, 100 μg, 500 μg, or 1 g.

According to the methods of the invention, the subject, individual, or patient can be any organism to whom the treatment is administered. Thus, the subject may be a human or other mammal, including, but not limited to a rodent (e.g., mouse, rat, rabbit), a canine (e.g., a dog), a feline (e.g., a cat), an equine (e.g., a horse), an ovine (e.g., a sheep), a porcine (e.g., a pig), or a bovine (e.g., a cow or steer). The subject can be any other animal such as a bird, reptile, amphibian, or any other companion or agricultural animal.

The method can be practiced in vivo as either a therapeutic method of treating a disease or disorder involving Aβ channels or as a prophylactic method to prevent the formation and/or operation of Aβ channels. In embodiments where the method is a method of treating (i.e., a therapeutic method), the amount is an amount that is effective for reducing or eliminating a cytotoxic effect associated with Aβ channels in the cells of the subject. The subject, individual, or patient may be one who is in immediate or apparent need of, or suspected of being in need of, treatment for a disease or disorder associated with Aβ channels. In such situations, where a pre-existing condition related to cell, tissue, or organ damage due to Aβ channels is evident or suspected, the method is a therapeutic method. For example, if a subject has symptoms of Alzheimer's disease, it may be beneficial to treat the subject with the compositions disclosed herein to arrest the progress of the disease.

In addition, according to the disclosed methods, the subject, individual, or patient may be one who is not in or suspected of being in need of treatment of a pre-existing disease or disorder. In such situations, the method is a prophylactic method. Prophylactic methods are useful in situations where the patient has a likelihood of developing a disease or disorder associated with Aβ channels. Thus, the present methods are useful not only for treating patients with a disease or disorder, but for treating patients who are suspected of having a predisposition to a disease or disorder. For example, if the family of a subject has been shown to be prone to a certain disease, the subject may be given the compositions of the invention to avoid or reduce the effects of that disease. Therefore, the disclosure provides a method of treating a subject who is suspected of having a predisposition to a disease or disorder, comprising administering to the subject an amount of the composition described herein sufficient to prevent Aβ-induced toxicity to the subject.

The methods disclosed herein generally comprise contacting at least one cell with at least one substance having a histidine coordinating capacity, such as the polypeptides described herein. The methods thus can be practiced in vitro, in vivo, and ex vivo. They accordingly may be practiced, for example, as a research method to identify compounds or to determine the effects of compounds and concentrations of compounds, as a therapeutic method of treating a disease or disorder involving Aβ channels, and as a method to prevent a disease or disorder. In embodiments where the method is a method of treating, it can be a method of therapy (e.g., a therapeutic method) in which the amount administered is an amount that is effective for reducing or eliminating a disease or disorder. In embodiments where the method is a method of prevention, the amount is an amount sufficient to prevent the disease or disorder from occurring or sufficient to reduce the severity of the disease or disorder if it does occur or to arrest the progress of the disease.

The methods can also be practiced in vitro. For example, the step of administering to at least one cell at least one compound having a histidine coordinating capacity, such as the polypeptides described herein, can occur in a petri dish, a test tube, an IV tube, or any other container applicable for contacting. When practiced in vitro, it may be a method for identifying parameters that are useful in in vivo treatment regimens. The method can be practiced to study the effects of combinations of the compositions disclosed herein with drugs on cells. For example, the compositions of the invention can be combined with other known drugs used for a disease, such as Alzheimer's disease. The in vitro methods can also comprise using the compositions to observe the effects of disruption of Aβ channels on cells or observe the cells for changes in protein expression, cell morphology, or any other characteristic of interest.

As used herein, a "sufficient amount" is an amount of a substance (e.g., a drug or compound) that produces a decrease in at least one detectable characteristic of a disease or disorder. For example, it may reduce the flow of current through an Aβ channel. It also may reduce the Aβ-induced toxicity in a cell. It further may prevent the formation of Aβ channels. Other characteristics can be immediately envisioned by those of skill in the art, and thus need not be listed herein. A sufficient amount of a substance can be administered in one or more administrations, in one or more doses. An amount sufficient to produce a detectable change, such as a detectable decrease, is typically an amount that provides a significant change in the levels of the characteristic of interest. In some instances, the change is a substantial change, such as a substantial decrease in the flow of current through an Aβ channel or a substantial decrease in the Aβ-induced toxicity in a cell. Changes can be measured relative to untreated control cells or any other appropriate negative control.

In embodiments, the method of treating comprises administering to a subject at least one compound having a histidine coordinating capacity, such as the polypeptides described herein, that affects Aβ channels involved in a disease or disorder, where the compound(s) are administered in an amount sufficient to reduce or eliminate the disease or disorder. As with other methods of treating described herein, the act of administering may be repeated one or more times to achieve a desired effect. Thus, each dose or dosing of a substance, etc. need not provide a sufficient amount of the compound, etc. to achieve the desired goal, but rather the cumulative dosage may, in embodiments, provide the sufficient amount to achieve the desired goal.

The act of administering the compound(s) can be any act that provides the compound(s) to the body of the subject so that they can function for their intended purpose. The compounds, etc. can be administered by any suitable route, in any suitable amount, and by way of any suitable regimen. Thus, the compounds can be, for example, administered orally, as a pill, capsule, caplet, powder, liquid, gel, salve, cream, lozenge, tablet, or any other suitable oral delivery vehicle. The compounds can also be delivered, for example, in an injectable or infusible form, such as a liquid suitable for intravenous injection or infusion or injection directly into a body site, subcutaneously, and intramuscularly. Alternatively, the compounds can be formulated, for example, to be absorbed via mucosal membranes or skin, and thus can be in a salve, cream, gel, or the like for topical, intranasal, sublingual, intrarectal, or intravaginal delivery. Amounts to be administered will vary depending on the administration route. One of skill in the art is capable of determining the appropriate amount of compound to be administered to a subject in need based on well-understood principles of pharmacology. The amounts and number and frequency of repetitions of administrations may be adjusted, according to well known principles of medicine, after one or more administrations or doses, in consideration of both the beneficial effects and deleterious effects (e.g., side-effects) of the compound(s) on the patient.

In a final aspect, the present compounds and compositions comprising the same can be used in methods to identify Aβ channels. Because the compositions of the invention interact with Aβ channels by forming coordination complexes with His residues in Aβ subunits of the Aβ channel, the compositions can be used to identify the presence of Aβ channels. Compounds in the composition can be labeled, contacted with a cell thought to contain Aβ protein channels, and the Aβ protein channels can be detected by immunodetection, fluorescence, or any other labeling system known in the art. Therefore, the disclosure provides a method of identifying the presence of at least one Aβ channel, comprising contacting a biological sample with a composition comprising a compound having a histidine coordinating capacity, such as the polypeptides described herein, in an amount sufficient to detect the presence of at least one Aβ channel in the biological sample. In one embodiment, the composition comprises a polypeptide having at least 2 but no more than 6-10 amino acid residues, wherein at least 2 but no more than 4 of those amino acid residues are histidine, wherein the polypeptide is not a fragment of the Aβ protein, and wherein the Aβ protein has the amino acid sequence of SEQ ID NO: 1. In another embodiment, the composition comprises a polypeptide consisting of four histidine residues. In yet another embodiment, the composition comprises a peptide consisting of two histidine residues. In certain embodiments, the biological sample comprises cells or tissue.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

EXAMPLES

The invention will be further explained by the following Examples, which are intended to be purely exemplary of the invention, and should not be considered as limiting the invention in any way.

Example 1

$Ni^{2+}$ and Imidazole can Efficiently Block Aβ Channels Incorporated in Artificial Membranes The detailed exemplary disclosure that follows, and particularly the experiments and data, were based on materials and methods that are disclosed in this Example, unless otherwise noted.

Planar Lipid Bilayer Methodology: A suspension of palmitoyloleoyl phosphatidylserine and palmitoyloleoyl phosphatidylethanolamine, (Avanti, Alabaster, Ala.) 1:1, in η-decane was prepared. This suspension was applied to an orifice of about 100-120 μm in diameter with a Teflon film separating two compartments, 1.2 ml volume each. The ionic solutions in the compartments contained asymmetrical concentrations of CsCl (200cis/50trans mM) and symmetrical 0.5 mM $CaCl_2$ and 5 mM K-HEPES, pH 7. The two ionic compartments were electrically connected to the input of a voltage clamp amplifier. Current was recorded using a patch clamp amplifier and data were stored on computer disk memory. Off-line analysis of the channel activity was carried out using the software package pClamp (Axon Instruments, Foster City, Calif.). Incorporation of Aβ peptide into the bilayer was obtained by adding an aliquot of proteoliposome (Aβ-liposome) suspension to the solution in the cis side of the planar lipid bilayer chamber and stirring.

Preparation of Proteoliposomes: Liposomes were prepared by hydration of air-dried palmitoyloleoyl phosphatidylserine (10 mg) with 1 M potassium aspartate, pH 7.0 (1 ml), followed by water sonication for 5 min. The liposome suspension (50 μl) was mixed with a stock aqueous solution of Aβ peptide (1 mg/ml, obtained from Bachem, Torrance, Calif. and from AnaSpec, San Jose, Calif.), followed by sonication.

Materials and His-related compounds: $NiCl_2$, imidazole and L-histidine were purchased from Sigma-Aldrich (St. Louis, Mo.). The histidine-related compounds NAHIS01 (Ac-His-CONH2), NAHIS02 (Ac-His-His-CONH2), and NAHIS04 (Ac-His-His-His-His-CONH2; SEQ ID NO: 2), which contain one, two and four His residues respectively, were synthesized as amide and capped in the amino terminal with acetic anhydride. NAHIS02-(π-Met) (Ac-His-π-Met-His-π-Met-CONH2) was synthesized by combining Fmoc-His(3-Me)-OH (Fmoc-His(π-Me)-OH, Bachem, Calif., USA), which possesses the imidazole group methylated at the π position.

Based on the theoretical model proposed by Durell et al. (1994), the predicted pore region of the Aβ channel is made of the hydrophilic structure composed of residues 1-16. The structure formed by a radial polymer of four to six Aβ subunits predicts that rings of His residues surround and form the path for the ions passing through the pore. Previous work (Diaz et al., 2006; Tickler et al., 2005) has shown that Aβ peptides can block Aβ channels. Since Aβ peptides all possess in their sequence the two vicinal His residues that have been modeled as lining the entry to the pore, it is possible that compounds of known His coordinating capacity will interact with His in the mouth of the pore. This interaction will block the entrance to the Aβ pore, and consequently affect the flow of current through the Aβ channel. Therefore, various compounds of known His coordinating capacity were studied for their interaction with Aβ channels incorporated into planar lipid bilayers. No membrane potential difference was applied to the lipid bilayers, to avoid any disturbing effect the membrane potential may have on the channel activity and in the conformations of the channel.

FIG. 1 illustrates the chemical structure of several His-related compounds. His is an aromatic amino acid which contains a heteroaromatic imidazole ring available for interaction. To study the contribution of the imidazole ring in the His interaction with the Aβ ion channel, we investigated the channel blocking efficiency of a modified, end-capped His in which the imidazole is the sole group available for interaction (NAHIS01), two modified, end-capped His groups which possess a total of two imidazole side chains (NAHIS02), and four modified, end-capped His groups which possess a total of four imidazole side chains (NAHIS04; SEQ ID NO: 2).

Figures 2C, 2D:
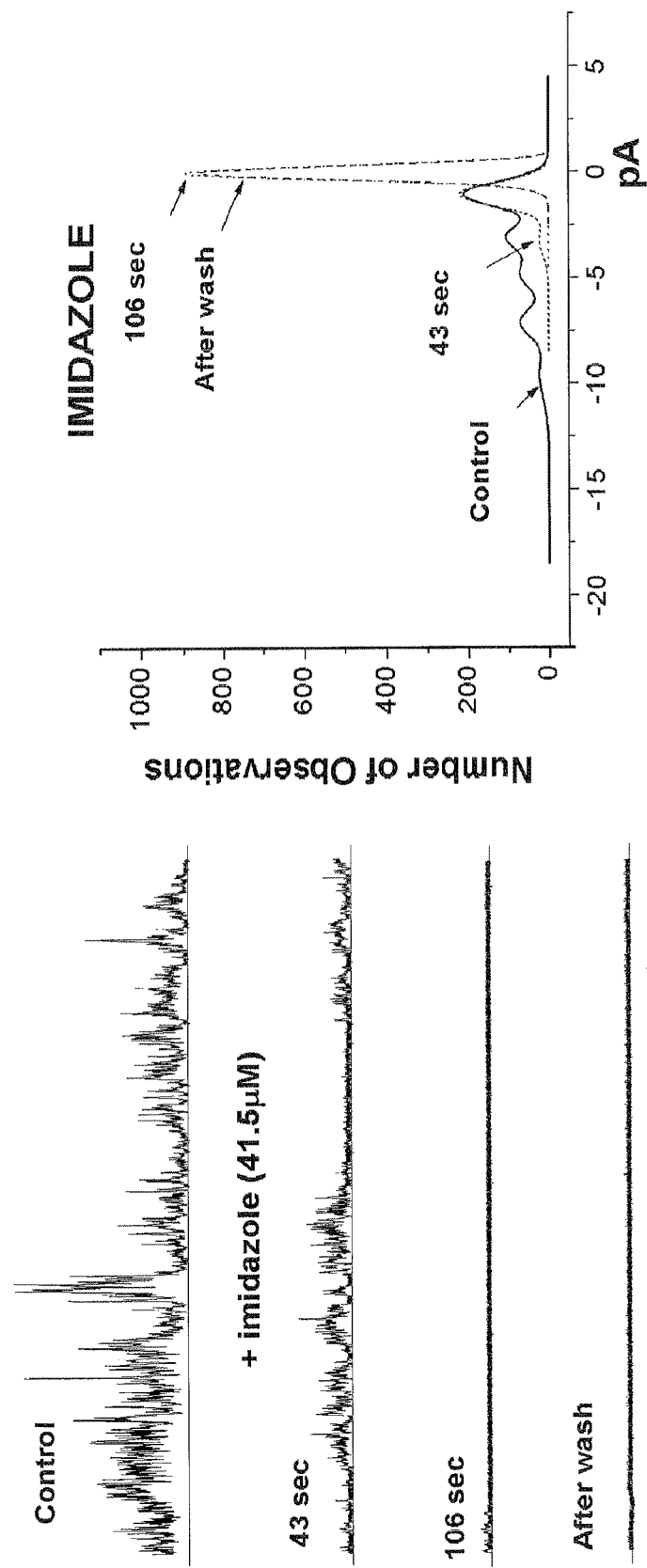

The experiments depicted in FIG. 2A show that when incorporated into a lipid bilayer, the Aβ channel operates between multiple conductance levels. One channel is responsible for the multiple conductance levels and each channel incorporation may show a different pattern of conductance transitions, as has been described elsewhere (Arispe et al., 1993; Arispe, 2004). The insert in FIG. 2A shows that discrete jumps of current to different levels, 1.46, 2.92, 5.03, 10.17 pA, can be observed throughout. The addition of $Ni^{2+}$, which coordinates with imidazole with high affinity, and imidazole, which has a preference to have an interplanar interaction with other aromatic residues, blocks the current activity of Aβ channels incorporated in lipid bilayers. After the ionic current through the incorporated Aβ channels appeared stable for several minutes, either $Ni^{2+}$ or imidazole was added to the experimental chamber. The current records in the figure display 8 seconds of activity from the Aβ channels, maintained at zero membrane potential, before (control) and several seconds after the channels were exposed to either $Ni^{2+}$ (FIG. 2A) or imidazole (FIG. 2C). The channel activity slowly reduced to an undetectable level, suggesting a full block of the channel. The blockage by both $Ni^{2+}$ (not shown) and imidazole (bottom record of FIG. 2C) was irreversible since the channels remained fully blocked after washing the chamber. Amplitude histograms of the current events during same time intervals of channel activity before and at different times after the addition of the test compounds were elaborated and are displayed in the right panels, FIGS. 2, B and D. The histograms show that both $Ni^{2+}$ and imidazole are effective in quickly abolishing the number of observations of the most frequent peak current values (0.8, 3.2, 5.2, 7.5 and 10 pA).

The highly effective block of the Aβ channels observed in our experiments after the application of either nickel ($Ni^{2+}$) or imidazole supports the hypothesis that the His in the Aβ subunits of the Aβ channels are the participating residues. Information collected from the Protein Data Bank reveals that among the aromatic residues His can be found in various chemical environments in protein structures, sometimes behaving as an aromatic residue, or as a metal ligand, and at other times forming salt bridges with acidic groups (Bhattacharyya et al., 2003). The interaction between His and $Ni^{2+}$ is so profound that the His tag is globally the most used tag in the preparative purification of proteins. Immobilized metal affinity chromatography, which is used to purify His-tagged proteins, exploits the ability of His to bind chelated transition metal ions, and $Ni^{2+}$ has generally been proven to be the most successful of the metal ions. Competitive interaction is the most common method used to recover the purified protein fractions. Imidazole competitively interacts with immobilized $Ni^{2+}$ ions to reverse the binding of the protein.

With the exception of nickel, the compounds that we found in this investigation to be efficient for blocking the Aβ channels were aromatic residues containing the heteroaromatic imidazole ring. As a heteroaromatic moiety, imidazole can interact with other aromatic and nonpolar groups, since it can exist in the neutral or positively charged form at the physiological pH. Additionally, imidazole can form the most conspicuous hydrogen bonds with polar and charged (both negative and positive) residues (Scheiner et al., 2002; Saha et al., 2005). Depending on the protonation state, imidazole can also be involved in salt-bridges with acidic groups. For these reasons, it is expected that effective interactions can be established between the imidazole-containing compounds that block Aβ channels and the charged $His^6$, $His^{13}$, $His^{14}$, $Glu^{22}$ and $Lys^{28}$ residues in the Aβ subunits in the Aβ channel. However, among the charged residues in the Aβ subunit sequence, His is the only aromatic residue and is the most likely candidate to carry the preferred face-to-face geometric interactions with imidazole (Bhattacharyya et al., 2003). Imidazole is a five-membered planar ring that consists of one π electron from the =N— atom, one from each carbon atom, and two from the NH nitrogen. This resonance structure makes imidazole an excellent nucleofile that would be attracted to a full or partial positively charged form of the His in the Aβ subunits of the Aβ channels. Therefore, the propensities of imidazole to interact with His residues vastly overcome the propensities to interact with the other charged residues, such as Lys or Glu, in the Aβ subunit (Bhattacharyya et al., 2003; Saha et al., 2005; Chakrabarti and Bhattacharyya, 2007).

In the case of the His-related compounds tested for blocking the Aβ channel, we observed a remarkable increase in blocking efficiency because the blocker compounds possess more available reactive imidazole side chains. In contrast, NAHIS02, which behaved as a highly efficient blocker, not only lost its capacity to block the Aβ channels, but additionally became ineffective in protecting from Aβ cytotoxicity, when the imidazole side chains were perturbed by methylation. A large number of studies have dealt with the subject of aromatic-aromatic interaction in proteins. The vast majority of medicinal agents contain aromatic substituents and their differential recognition by proteins is likely to be facilitated by the noncovalent interactions involving aromatic residues (Gilman et al., 1993). Among the aromatic residues, His has the highest propensity to interact with planar groups and forms a distinct class separate from all other residue types (Saha et al., 2005: Chakrabarti and Bhattacharyya, 2007).

Example 2

NAHIS01 is More Effective at Channel Blocking than Unmodified His

To study the contribution of the imidazole ring in the His interaction with the Aβ ion channel, we investigated the channel blocking efficiency of a modified, end-capped His (NAHIS01) and compared it with the blocking efficiency of the unmodified, amino and carboxyl ends-free His. The end-capped His, with the carboxyl and amine group amidated and acetylated, respectively, would leave the imidazole side chain as the sole group available for interaction with other reactive groups in the Aβ channel.

Figures 3A, 3B:
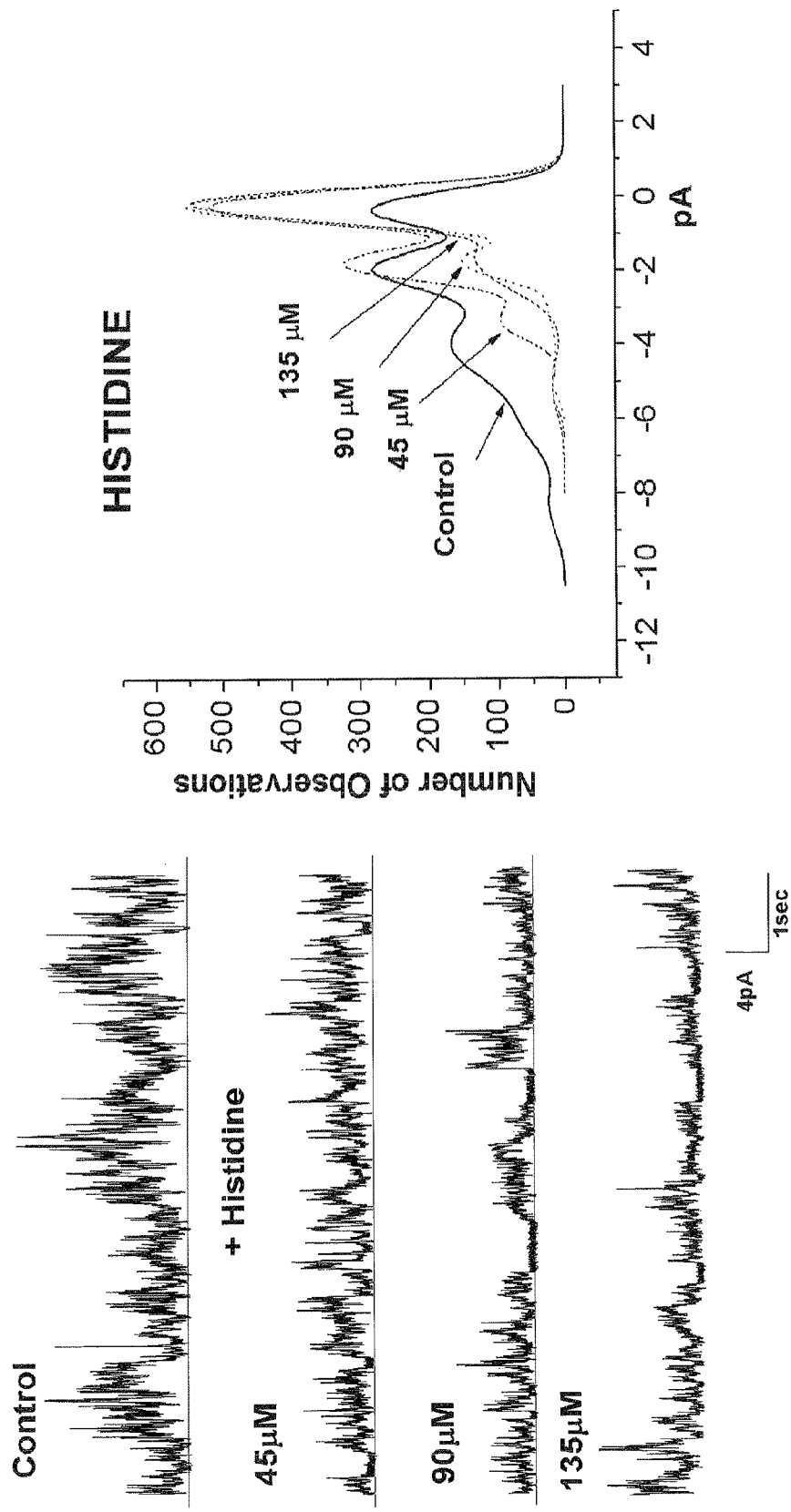
FIG. 3 shows that the efficacy of His to block the Aβ channel is improved by capping its amino and carboxyl ends. (A and C) Electrical activity from two lipid bilayers with incorporated Aβ channels, recorded before (control) and while the Aβ channel was exposed to various concentrations of unmodified, amino and carboxyl ends-free His, and a modified His, NAHIS01, with the carboxyl and amine groups amidated and acetylated. The Aβ channels were exposed to each concentration of the blocker compounds for 2-min periods. Increases in the concentration of the unmodified His only affect the current peaks of 5.8 and 4.2 pA, corresponding to larger channel conductance. NAHIS01 is more effective at reducing all current peaks at much lower concentrations than unmodified His. B and D display the amplitude distribution histograms of the ionic current peaks recorded while the Aβ channel was exposed to each concentration of His and NAHIS01, respectively.
Figures 3C, 3D:
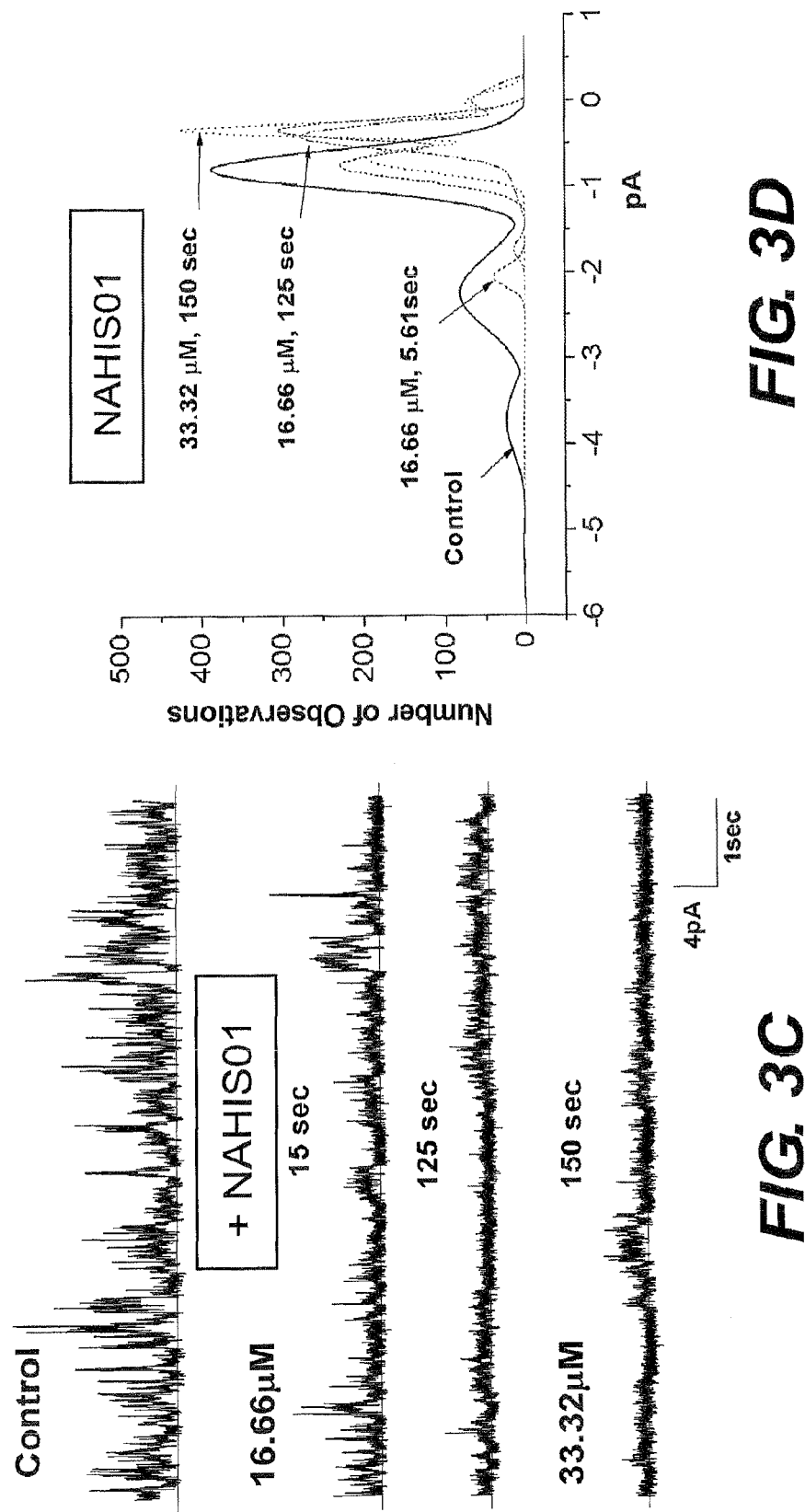

The current activity from Aβ channels illustrated in FIG. 3 indicates that both unmodified His, and modified His NAHIS01 affect the peaks of ionic current from an Aβ channel incorporated in a lipid bilayer. The current records in FIGS. 3, A and C, and the current amplitude histograms in FIGS. 3, B and D, show that unmodified His mildly reduces the Aβ channel activity and is relatively ineffective at producing an irreversible full block of the Aβ channels. The peaks of ionic current corresponding to larger channel conductance (5.8 and 4.2 pA) are blocked in a concentration-dependent manner, but the smaller current peaks remain unaffected at the highest concentration of His. As shown in FIGS. 3, C and D, although the modified His NAHIS01 did not operate as a full channel blocker, it more effectively reduced the Aβ channel activity at lower concentrations.

This example shows that the efficacy for blocking the Aβ channel by the amino acid His is improved when the free ends of His are modified by amidation and acetylation of the carboxyl and amine groups, respectively. This modification, in addition to making the peptide resistant to proteases degradation, reduces the peptide unspecific reactivity. Our interpretation of the improved blocking efficacy of NAHIS01 compared to the ends-free His is that in the unmodified His, in addition to the imidazole side chain, the free ends increase the possibility for His to unspecifically interact with any other reactive residues present in the Aβ subunits of the Aβ channel. Therefore, the unspecific interactions with other regions of Aβ reduce the probability of specific interactions with His that form the ion-conducting path of the Aβ channel. When the His ends are capped and are unable to chemically react, as is the case in NAHIS01, the reactivity of His is restricted to the specific interaction that may be established by its imidazole side chain. Thus, the probability for aromatic interactions between the exceptionally nucleofilic imidazole in the ends-capped His and the imidazole side chain in the participating His in the Aβ channel will be increased. We believe that the improved efficacy of the ends-capped NAHIS01 compared to ends-free His, as an Aβ channel blocker, is further proof of the concept that the aromatic interaction between the imidazole side chains contributes to the blocking of Aβ channels.

Example 3

The Aβ Channel Blocking Efficiency of His-Related Compounds Increases with the Number of Imidazole Side Chains In the previous experiments we showed that NAHIS01, in which the imidazole is the sole group available for interaction, is very efficient at blocking the Aβ ion channel. Here we studied the ability of two His-related compounds, NAHIS02 and NAHIS04, to block Aβ channels. NAHIS02 and NAHIS04 are also comprised of end-capped histidines, with the carboxyl and amine group on the terminal histidines amidated and acetylated, respectively. This would leave two (NAHIS02) and four (NAHIS04) imidazole side chains as the sole groups available for interaction with other reactive groups in the Aβ channel.

Figures 4A, 4B:
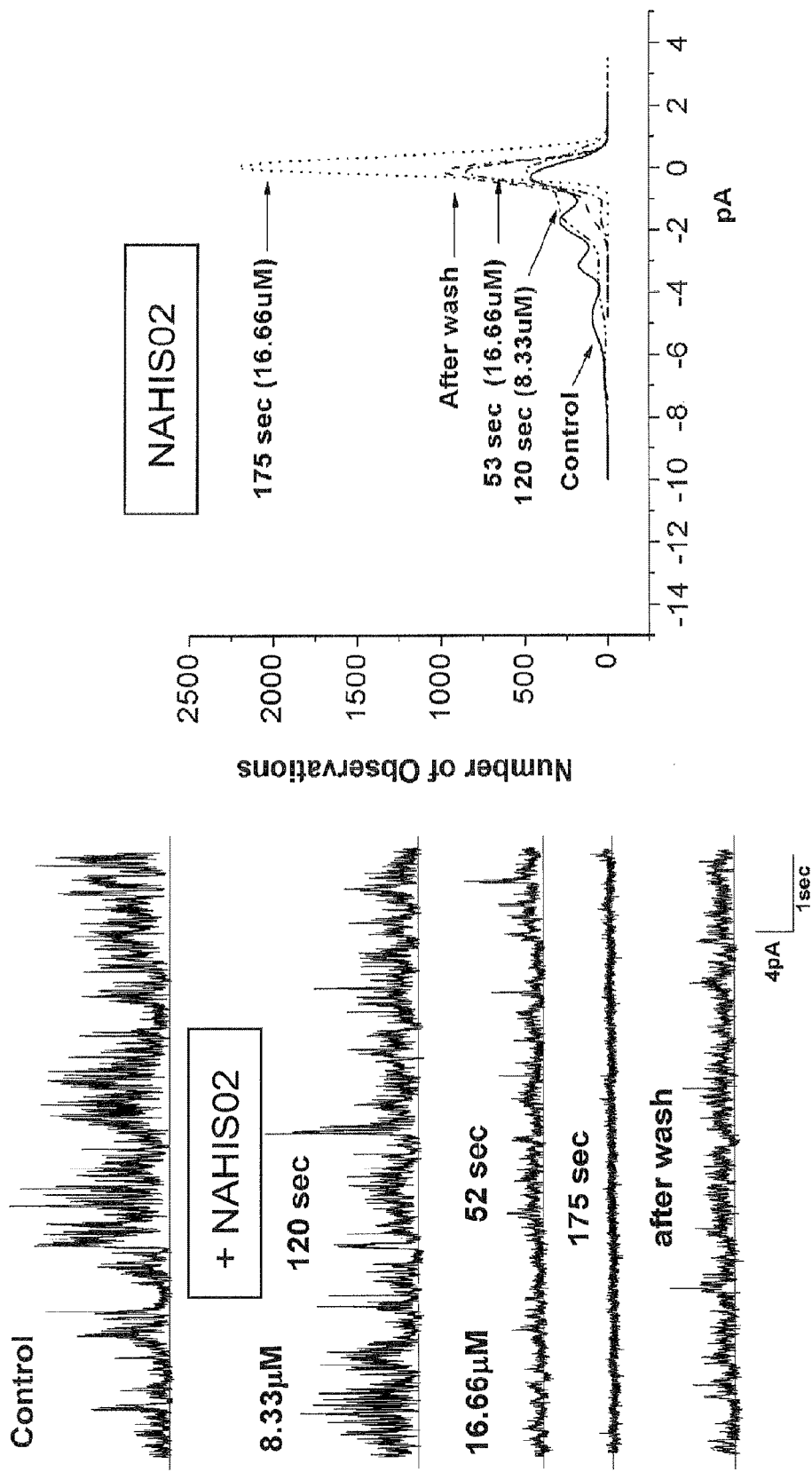
FIG. 4 depicts that Aβ channel blocking efficiency of His-related compounds increases with the number of imidazole side chains. (A and C) Electrical activity from two lipid bilayers with incorporated Aβ channels, recorded before (control) and while the Aβ channels were exposed to two compounds that possess two (NAHIS02) and four (NAHIS04) imidazole side chains, respectively. The current records show the channel activity at various times after the channels were exposed to two concentrations of the blocker compounds. After full blockage of the Aβ channel, the blocking action of NAHIS02 reversed when the experimental chamber was washed of the blocker. The blockage by NAHIS04 was irreversible. B and D display the amplitude distribution histograms of the ionic current peaks recorded while the Aβ channel was exposed to various concentrations of NAHIS02 and NAHIS04, respectively. At a concentration of 16.66 µM both compounds removed all current peaks. However, NAHIS04 produced full blockage more quickly.
Figures 4C, 4D:
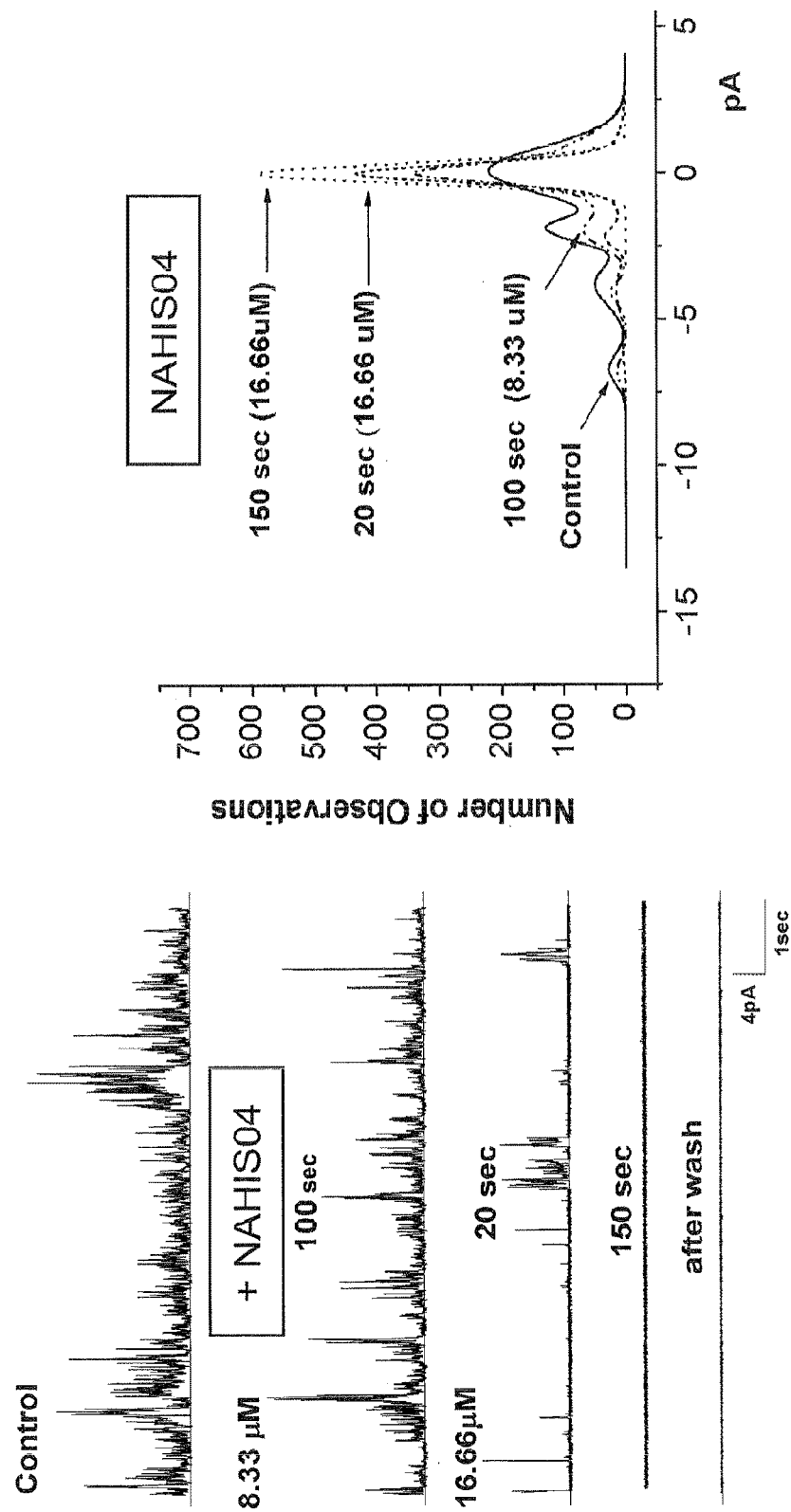

The current records and current amplitude histograms from Aβ channels, before and after exposure to the two His-related compounds, are illustrated in FIG. 4. During the current recording, the bilayer was maintained at zero membrane potential. The current records in FIGS. 4, A and C, show that both compounds efficiently block the multiple conductances exhibited by the Aβ channels. However, one of the distinguished observations is an apparent higher affinity by NAHIS04 for the channel that stayed fully blocked after the chamber was washed. The lower current record in FIG. 4C shows that NAHIS04, which possesses four imidazole side chains, is the most effective at irreversibly blocking the Aβ channel activity. The lower current record in FIG. 4A shows some recovery of channel activity after NAHIS02 was washed off. No effect of membrane potential in the blocking capacity of these compounds was observed (not shown). We previously reported that the level of the membrane potential has no effect on the ability of similar His-related compounds to block the Aβ channel (Arispe, 2004). The current amplitude histograms in FIGS. 4, B and D, show a gradual reduction in the number of current peaks after the Aβ channels are exposed to either one of these His-related compounds. The results reveal that the number of imidazole side chains in the blocker compounds has a substantial influence in their efficiency for blocking the Aβ channel conductance. The experiment illustrated in FIG. 4C shows that NAHIS04 (16.66 μM), which possesses four imidazole side chains, reduced the Aβ channel activity to occasional channel openings just 20 sec after addition. By contrast, the same concentration of NAHIS02, which possesses two imidazole groups, takes several minutes to produce similar levels of channel blockage.

Figure 5A:
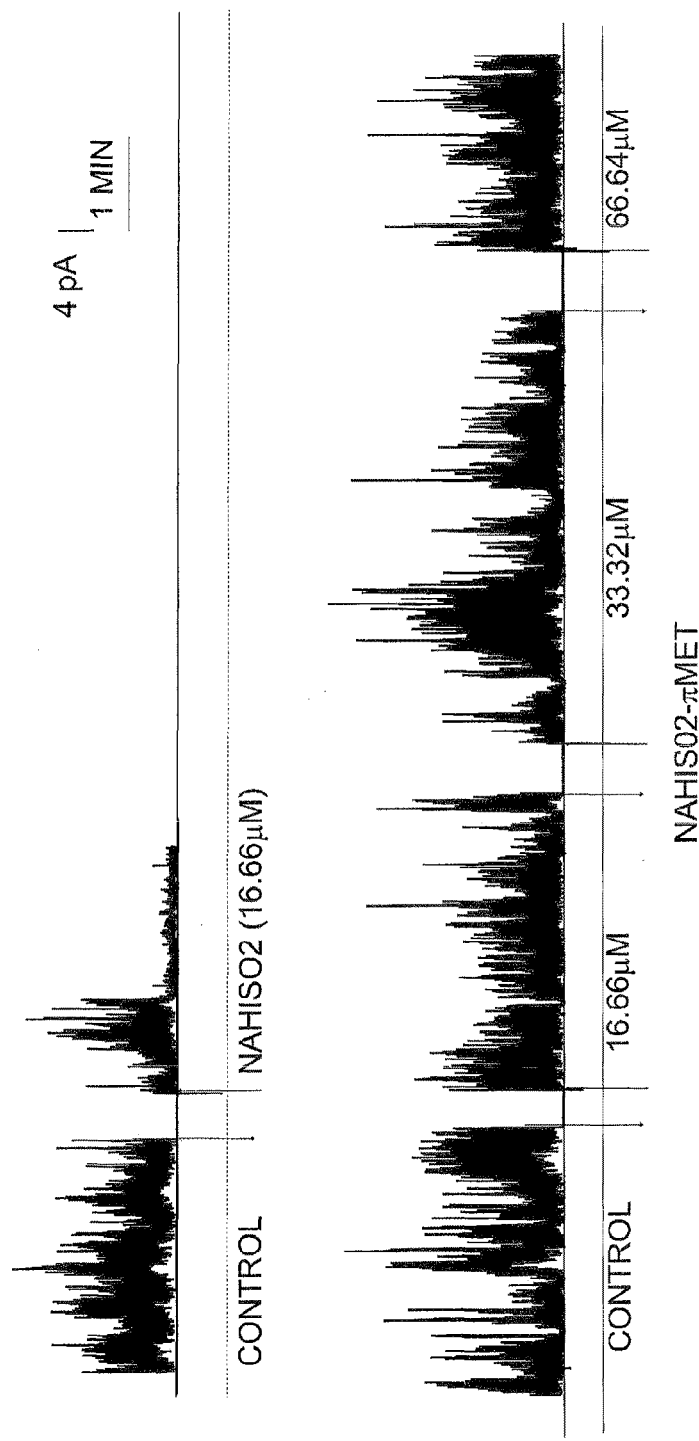
FIG. 5 illustrates a time course of ionic charge conducted by membrane-incorporated Aβ channels, showing the effect of Aβ channel blockers. (A) The current records show the time course of the activity of Aβ channels incorporated into planar lipid bilayers before and after the addition of the Aβ channel blocker NAHIS02 (top record) and NAHIS02-(π-Met) (bottom record). The concentration of NAHIS02-(π-Met) was gradually increased as indicated, at the times signaled by the arrows. NAHIS02-(π-Met) did not affect the Aβ channel activity even at a fourfold higher concentration. (B) The amount of charge conducted by bilayer-incorporated Aβ channels before and after the addition of imidazole, $Ni^{2+}$, and His at concentrations of 41.5 µM (left plot), and NAHIS01, NAHIS02, NAHIS02-(π-Met), and NAHIS04 at a concentration of 16.6 µM (right plot). The ionic current flowing through the membrane was integrated in consecutive time intervals of 8-ms duration. The efficiency to stop Aβ channel activity increases as the number of imidazole side chains in the blocker compounds is increased. pC: picoCoulombs.
Figure 5B:
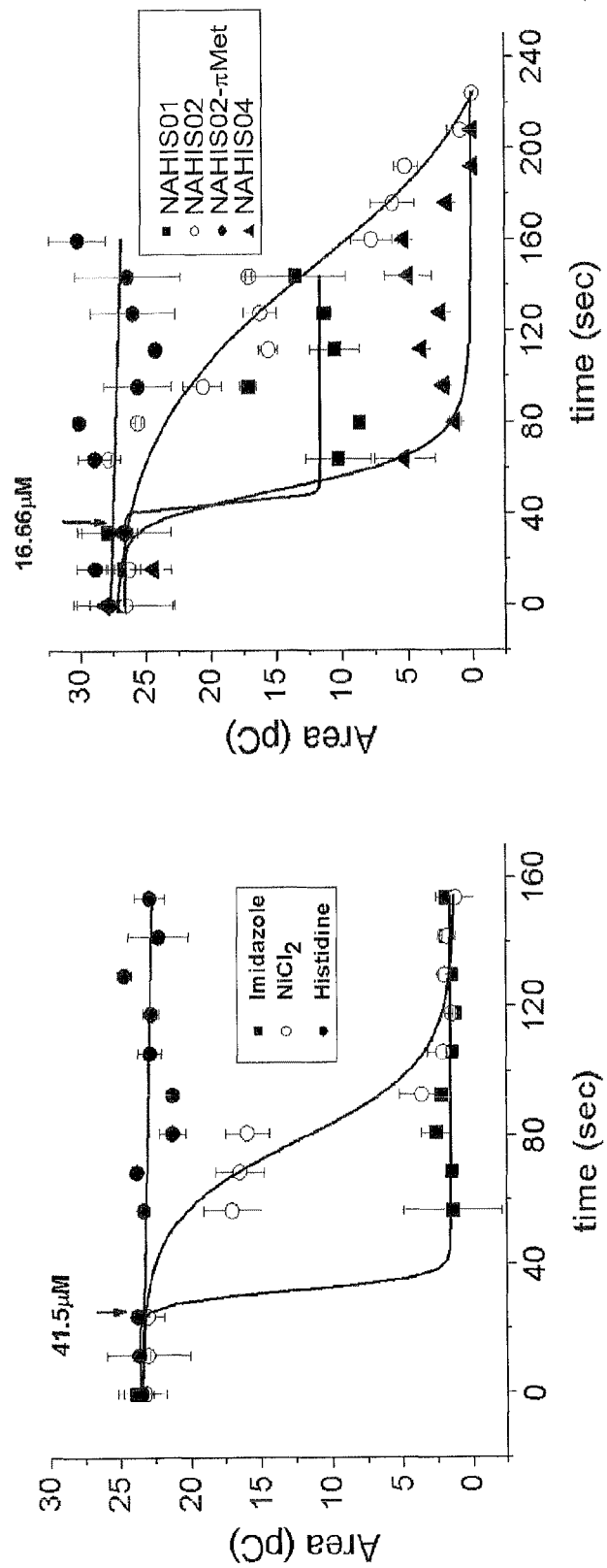

The contribution of the imidazole side chains in the His-related compounds to block the Aβ channel activity was verified with the experiments shown in FIG. 5. Here the effectiveness of the His-coordinating and His-related compounds was studied in terms of the time required to block the Aβ channel currents. The top current record in FIG. 5A displays the time course of the Aβ channel activity before and after the addition of the channel blocker NAHIS02. The bottom current record displays the channel activity from a similar experiment in which increasing concentrations of a modified NAHIS02, NAHIS02-(π-Met), were added. NAHIS02-(π-Met) is a modified NAHIS02 in which the imidazole side chains are methylated. The unmodified NAHIS02, at 16.66 μM, totally blocks the Aβ channel activity in less than three minutes. In contrast, NAHIS02-(π-Met) is unable to block the Aβ channel activity even at a fourfold higher concentration, indicating that the methylation of the imidazole groups reduces the affinity of NAHIS02 for the Aβ molecule and consequently the ability to block the Aβ channel. When Aβ channels are incorporated into artificial membranes, they form multi-conductance systems. This is manifested by frequently fluctuating conductance between specific levels. To comparatively evaluate the blocking strength of the test compounds in terms of the time required to stop the Aβ channel activity, experiments similar to that displayed in FIG. 5A were performed with each one of the test compounds. The results were analyzed by an alternative procedure that quantifies the total ionic current flowing through the Aβ channel incorporated into the artificial lipid membrane at any given time. For this purpose, we integrated the total ionic current flowing through the membrane and averaged the amount of charge conducted in consecutive time intervals of 8 msec duration. The integration was initiated after the incorporated channel had achieved stable activity, and also after the addition of the test compounds. The left panel plot in FIG. 5B shows that imidazole is extremely efficient at promptly (30 sec) blocking the flow of ionic charges, in contrast to His, which was very slow-acting or had almost no channel-blocking capacity. $Ni^{2+}$ ions, as also shown in FIG. 2A, fully blocked the Aβ channel within a few seconds (120 sec). The plot in the right panel in FIG. 5B shows that the efficiency for stopping the Aβ channel activity of the His-related compounds appears to increase as the number of imidazole side chains in the His-related compound is increased. Hence NAHIS04, which has four imidazole side chains, reduces the flow of ionic charges through the membrane by 50% in 15 sec. This reducing effect is eightfold faster compared to the 125 sec it takes for NAHIS02, which has two imidazole side chains, to achieve the same level of reduction. In contrast, NAHIS01, which only has one imidazole side chain, does not fully prevent the flow of ionic charges, and NAHIS02-(π-Met), from which imidazole reactivity is removed by methylation, showed no blocking capacity.

Example 4

Protection of Cells from Aβ Cytotoxicity Increases in Efficiency with the Number of Imidazole Groups in the Aβ Channel Blocker Cell culture: PC 12 cells, derived from a transplantable rat pheochromocytoma (ATCC # CRL 1721), were cultured in the recommended ATCC medium. Primary cultures of hippocampal and cortical neurons from P18-P21 rat brains were grown in neurobasal medium/B27 (GIBCO). For neurons preparation, pregnant rats were anesthetized and killed to extract the fetuses. For pain alleviation, the animals were anesthetized following recommendations in the 2000 Report of the American Veterinary Medical Association Panel on Euthanasia. Brains from the fetuses were dissected out and neuronal cell cultures prepared as in a previously described protocol (Simakova and Arispe, 2006).

Cell viability assays: The percentage of cells protected from Aβ-induced cell death by various treatments was evaluated by means of a colorimetric XTT assay (Cell Proliferation Kit II, Roche, Mannheim, Germany). The cytotoxicity was also directly measured by the release of lactate dehydrogenase (LDH) from the cytosol into the media (Cytotoxicity Detection Kit (LDH), Roche, Mannheim, Germany).

Figures 6C, 6D:
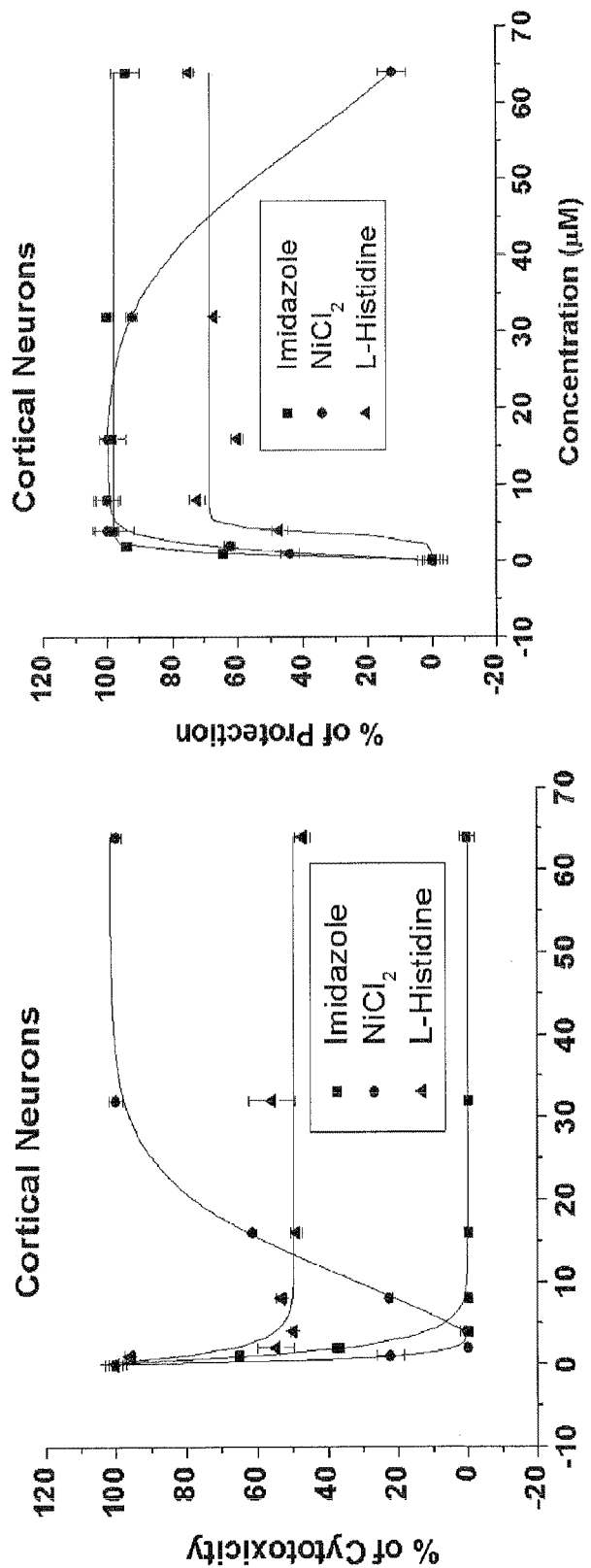
FIG. 6 shows the protection of cells from Aβ cytotoxicity by compounds that coordinate and associate with Aβ channels. Viability of PC12S cells (A and B), and cortical (C and D) and hippocampal neurons (E and F) observed after 3 days of incubation in the presence of Aβ peptide (5 µM) and Aβ peptide (5 µM) plus $Ni^{2+}$ imidazole, or His. The results from the XTT assay are expressed as a percentage of cytotoxicity (A, C, and E). The LDH released from cells into the media is expressed as a percentage of protection of cells (B, D, and F). Imidazole and $Ni^{2+}$ fully protect cells against Aβ cytotoxicity, but $Ni^{2+}$ showed a cell-dependent toxicity at high concentrations. His performed poorly in protecting cells from Aβ toxicity.
Figures 6E, 6F:
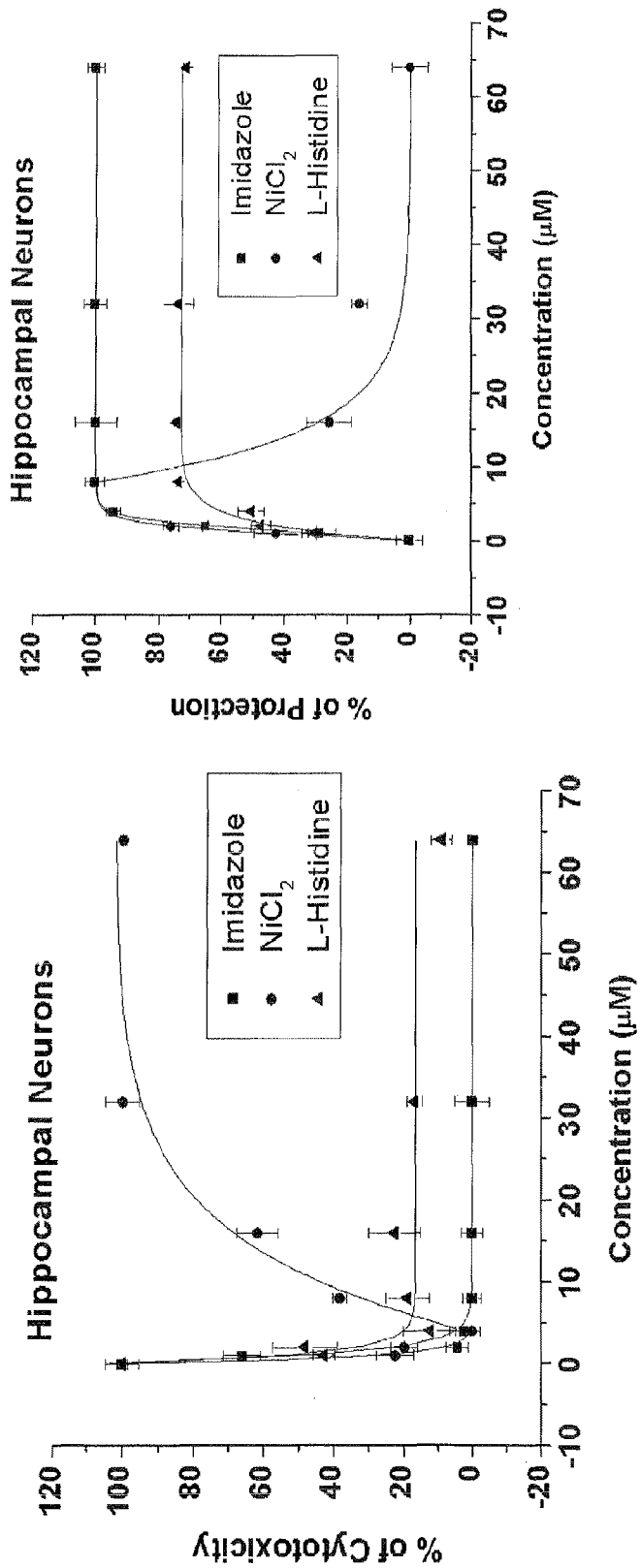
Figures 7A, 7B:
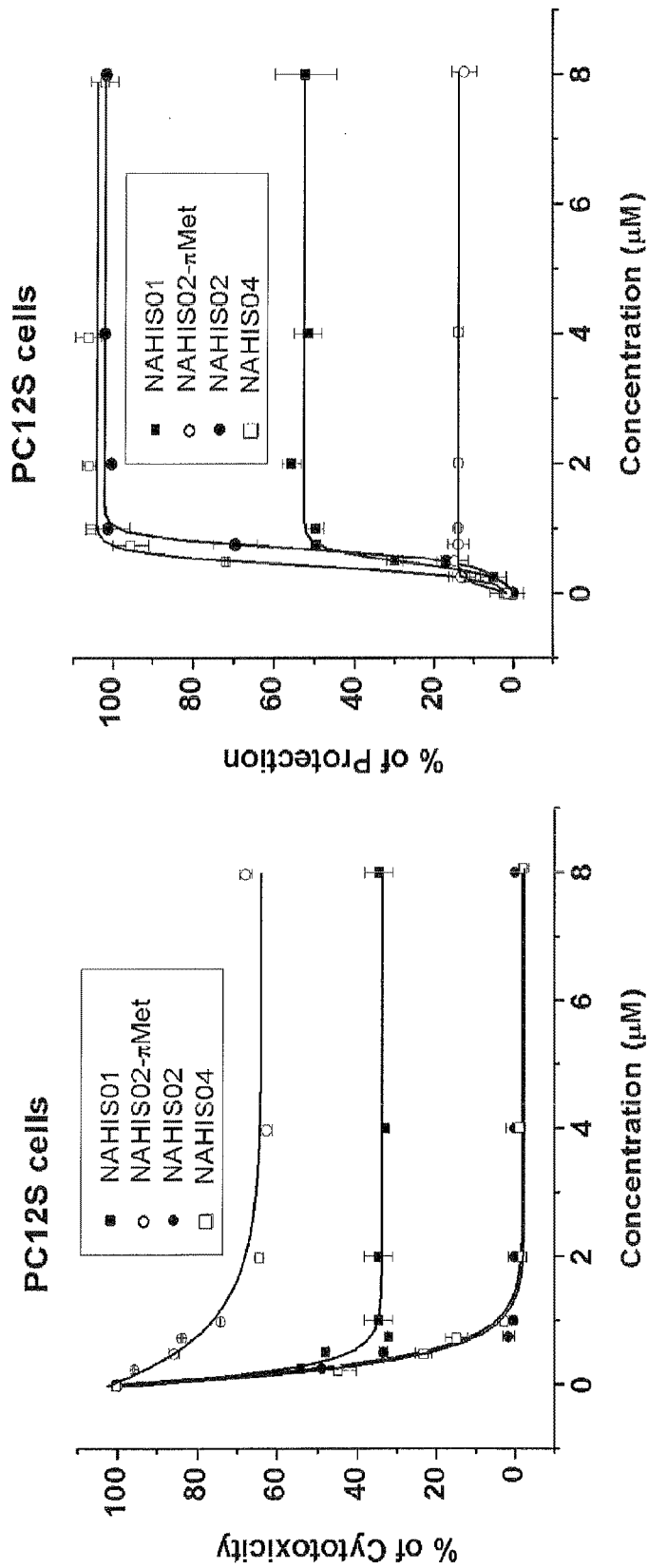
FIG. 7 depicts the protection of cells from Aβ cytotoxicity by His-related compounds that establish aromatic interaction with Aβ channels. Viability of PC12 cells (A and B), and cortical (C and D) and hippocampal neurons (E and F) observed after 3 days of incubation in the presence of Aβ peptide (5 µM) and Aβ peptide (5 µM) plus NAHIS01, NAHIS02, NAHIS02-(π-Met), and NAHIS04. The results from the XTT assay are expressed as a percentage of cytotoxicity (A, C and E). The LDH released from cells into media is expressed as a percentage of protection of cells (B, D and F). The level of protection for all these compounds correlated to the number of reactive imidazole side chains. NAHIS02 and NAHIS04 fully protected the cells against Aβ. NAHIS02-(π-Met) was very inefficient at protecting against Aβ peptide cytotoxicity.
Figure 7D:
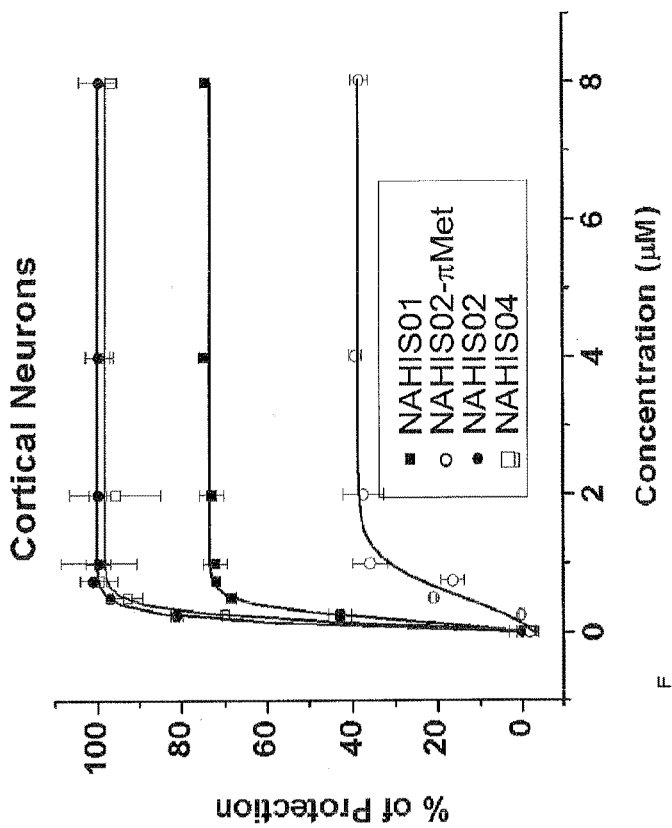
Figure 7C:
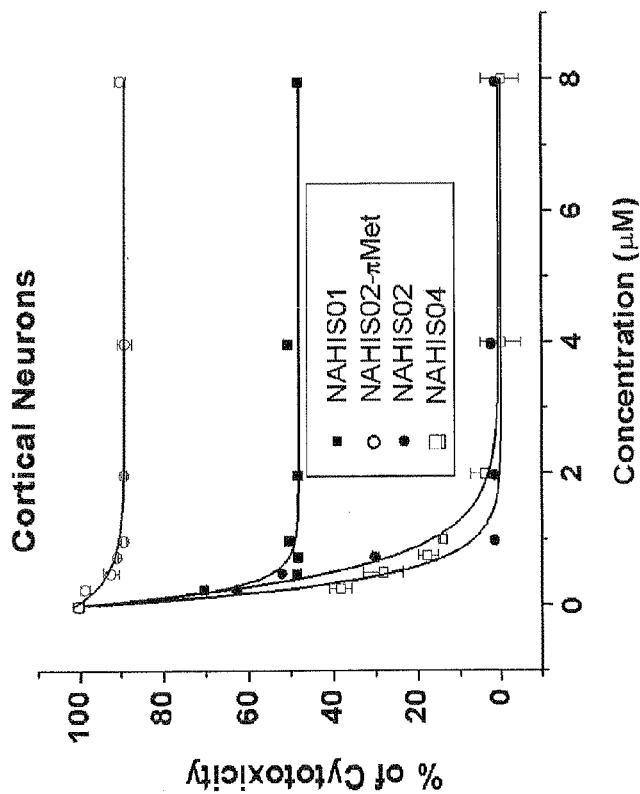
Figures 7E, 7F:
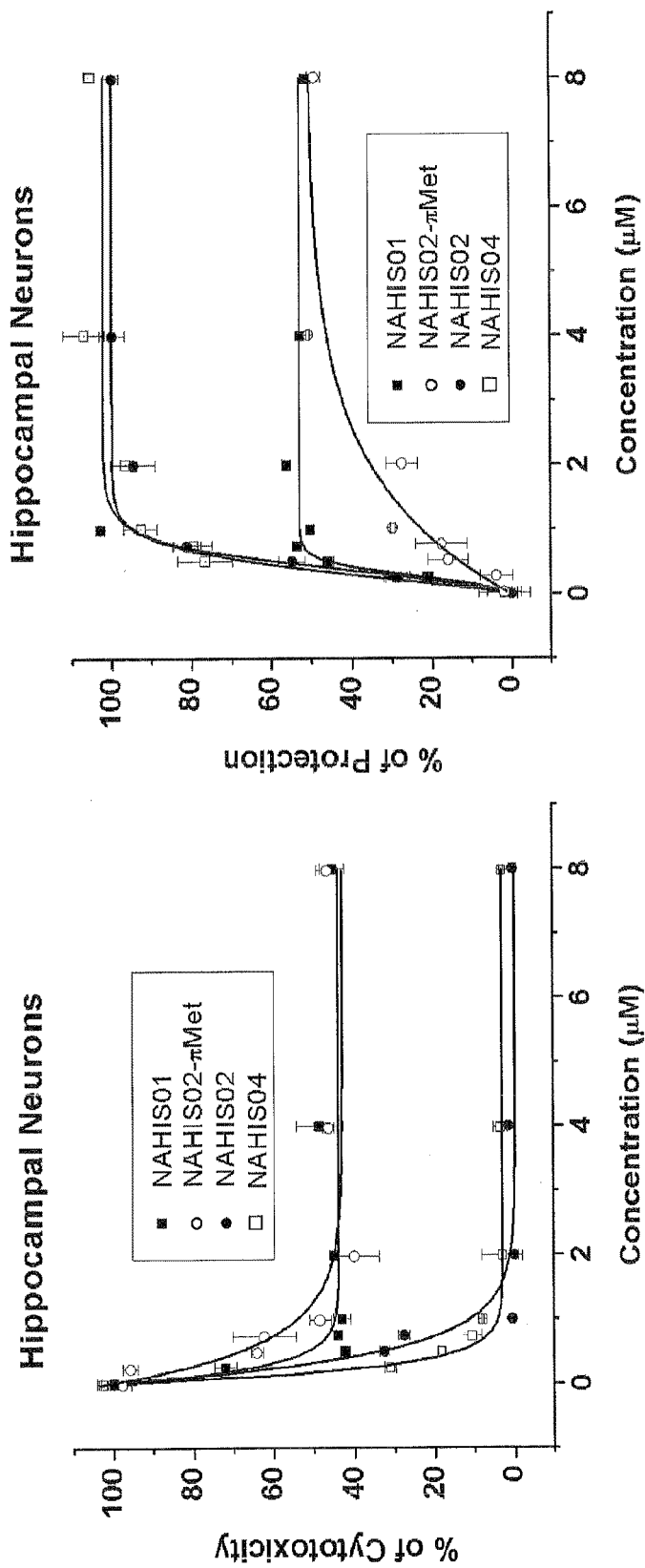

We have previously shown that Aβ cytotoxicity can be prevented when cells are incubated in media containing Aβ channel blockers (Simakova and Arispe, 2006; Arispe et al., 2007; Tickler et al., 2005). Since $Ni^{2+}$, imidazole, histidine and the His-related compounds affect, to different degrees, Aβ channels incorporated into artificial membranes, we examined the ability and relative strength of these compounds to protect cells from Aβ peptide-induced cell death. Cell viability was examined using two different assays. These were the colorimetric XTT assay that quantifies metabolically active cells, and an assay that measures the release of lactate dehydrogenase (LDH) from the cytosol into the media, which evaluates the cell membrane integrity. The panels in FIG. 6 show the viability of PC12 cells (A and B), and cortical (C and D) and hippocampal neurons (E and F)

observed after three days of incubation in the presence of Aβ peptide (5 μM) and Aβ peptide (5 μM) plus Ni$^{2+}$, imidazole or histidine. The left panels (A, C and E) show the results from the XTT assay expressed as a percentage of cytotoxicity, and the right panels (B, D and F) show the results from the measurements of LDH released from cells into the media expressed as a percentage of protection of cells. The performance of imidazole, Ni$^{2+}$ and His to maintain cell viability and protect cells from Aβ peptide-induced cell death strongly corresponds to what one would expect from their effects displayed on the ionic current flowing throw the Aβ channels incorporated into artificial membranes. Imidazole and Ni$^{2+}$ were found to fully protect the cells against Aβ cytotoxicity, but Ni$^{2+}$ showed a cell-dependent toxicity at high concentrations. On the other hand, His, which mildly reduced the Aβ channel activity, performed poorly in protecting cells from Aβ toxicity.

The panels in FIG. 7 show the viability of PC12 cells (A and B), and cortical (C and D) and hippocampal neurons (E and F), observed after three days of incubation in the presence of Aβ peptide (5 μM) and Aβ peptide (5 μM) plus the His-related compounds NAHIS01, NAHIS02, NAHIS02-(π-Met), or NAHIS04. The left panels (A, C and E) show the results from the XTT assay as percentage of cytotoxicity, and the right panels (B, D and F) show the results from the measurements of LDH release into the media as a percentage of protection of cells. The performance of the His-related compounds to protect cells from the Aβ peptide-induced cell death also strongly corresponded to what one would expect from their effects displayed on the ionic current flowing throw the Aβ channels incorporated into artificial membranes. NAHIS02 and NAHIS04 fully protected the three different types of cells against Aβ. NAHIS01, which did not fully block Aβ channels in artificial membranes (see FIG. 4), showed partial protection. The level of protection for all these compounds correlated with the number of imidazole side chains in these compounds. For instance, the concentration required for 50% protection (half maximal effective concentration, $EC_{50}$) for the three different types of cells for the compounds NAHIS02 and NAHIS04 was always below 1 The $EC_{50}$ for imidazole was between 2 and 3 μM (see FIG. 7). The compound NAHIS02-(π-Met) was very inefficient at protecting against Aβ peptide cytotoxicity. The mild protection observed with this compound was cell-type dependent and always plateaued at much higher concentrations than that observed with the unmethylated form. Full methylation of NAHIS02-(π-Met), is never achieved during the synthesis process. Therefore, a mild protection is not totally unexpected to be observed in the results. However, the loss of protection strongly suggests that the methylation is affecting at the site of the molecule that interacts with the Aβ channel.

The Examples described herein show that blocking Aβ channels preserve cells from Aβ cytotoxicity. The efficacy of His coordinating compounds to preserve cells from Aβ cytotoxicity was tested in three different types of cells. In other studies, the preservation of the viability of cells observed in cases where specific Aβ channel blockers were used in combination with Aβ confirmed the participation of the Aβ channels in Aβ cytotoxicity (Diaz et al., 2006; Simakova and Arispe, 2006). Those compounds that were observed to fully block Aβ channels incorporated into artificial membranes were also found to be efficient at preserving cell viability during exposure to the toxic Aβ peptide. The results were obtained from three different cell types by the application of two different viability assays. It has been shown that the interaction between Aβ peptides and the cell surface membrane is followed by activation of an intracellular signaling cascade that leads to the death of cells by apoptosis (Loo et al., 1993). The finding that Aβ channel blockers fully prevent cell death corroborates the formation of Aβ ion channels as the initial step in the changes associated with the Aβ-induced apoptosis (Simakova and Arispe, 2006), and suggests that channel formation is the main mechanism by which Aβ exerts its toxicity. Additionally, the data shown here confirm that exposure of cells to Aβ results in the formation of oligomeric Aβ aggregates, which assemble the Aβ channels as they interact with the cell surface membrane. This is the first step in the signaling cascade that leads to cell death. The results from the application of viability assays on the three different types of cells show that the efficacy of the His-related compounds to preserve cells from the Aβ cytotoxicity is correlated to the intensity of the interactions with the His residues in the Aβ channel. By increasing the number of reactive imidazole side chains in the blocker compound, the capacity to block the active Aβ channels incorporated into the membranes of the cells is also increased. Our results in cultured cells showed that the blocking efficacy of His-related Aβ channel blockers was improved to $EC_{50}$ values below the micromolar levels, as was the case for the blockers NAHIS02 and NAHIS04. This represents a considerable improvement compared to the blocking effect obtained with previously published Aβ channel blockers (Arispe, 2004; Arispe et al., 2007; Diaz et al., 2006).

Example 5

NAHIS04 is More Effective at Protecting Cells from Aβ Cytotoxicity Than NA4 and NA7

Figures 8A, 8B:
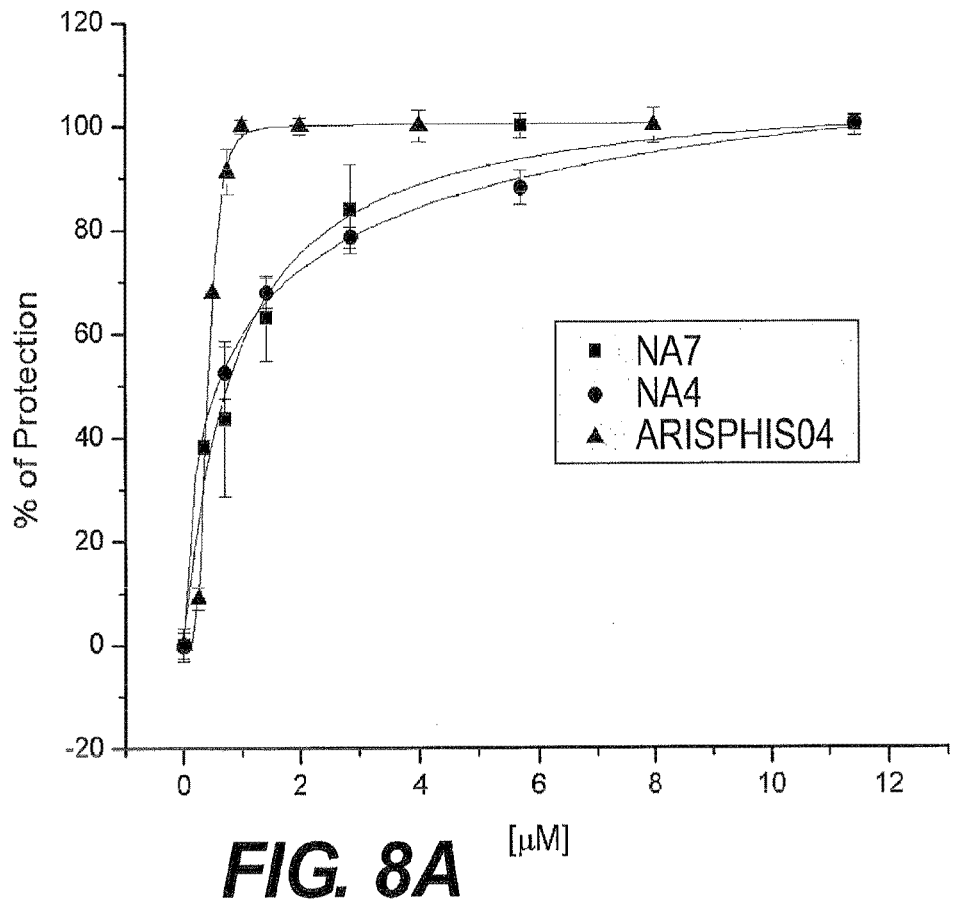
FIG. 8 depicts the protection of PC12 cells from Aβ cytotoxicity by either NA4, NA7 or NAHIS04 (Panel A) and the concentration required for 50% protection of the cells ($EC_{50}$; Panel B).

Previous studies have shown that the native peptide fragments from the Aβ polypeptide, NA4 (SEQ ID NO: 3) and NA7 (SEQ ID NO: 4), are able to block Aβ channel activity and protect cells from Aβ cytotoxicity. In this Example, NAHIS04, comprised of end-capped histidines, was compared to NA4 and NA7, both of which are not capped and do not have modified histidines. Cell viability was examined using the assay that measures the release of lactate dehydrogenase (LDH) from the cytosol into the media, which evaluates cell membrane integrity. FIG. 8A shows the viability of PC12 cells observed after three days of incubation in the presence of NA4, NA7 or NAHIS04. The His-related compound with the modified histidines, NAHIS04, showed better protection of the cells. The concentration required for 50% protection (half maximal effective concentration, $EC_{50}$) for NAHIS04 was less than 1 μM (Panel B). It was also between 2-3 times less than the $EC_{50}$ for either NA4 or NA7. This Example shows that NAHIS04 is able to protect cells against Aβ-induced cytotoxicity at much lower concentrations than either NA4 or NA7.

Example 6

NAHIS02 Loses the Capacity to Block Aβ-Induced Intracellular Calcium Increase and Protect Cells Against Aβ after Imidazole Methylation of its Histidine Residues Intracellular Free Calcium measurements: Cells were plated on glass cover slips coated with poly-L-lysine and loaded with 2 μM FURA-2AM (Molecular Probes) calcium sensitive probe in incubation buffer (135 mM NaCl, 5 mM KCl, 2.5 mM $CaCl_2$, 1.2 mM $MgCl_2$, 10 mM glucose, 10 mM Hepes, pH 7.4). After 30 min of loading period, cells were treated with Aβ (7.66 μM). The time course of changes in the emission from FURA-2AM was observed using an inverted epi-fluorescence/phase contrast microscope equipped with a low-light level integrating CCD camera+microphotometer assembly (InCy I/P-2 Imaging & Photometry System, Intracellular Imaging INC.)

Planar Lipid Bilayer Methodology and Preparation of Proteoliposomes: The experiments were performed as described previously except that the suspension of palmitoyloleoyl phosphatidylserine and palmitoyloleoyl phosphatidylethanolamine was applied to an orifice of about 80-100 µm in diameter with a Teflon film separating two compartments. In addition, the liposome suspension (50 µl) was mixed with a stock aqueous solution of Aβ40 (1 mg/ml; obtained from Invitrogen, Carlsbad, Calif.).

Aβ Cytotoxicity: PC12 cell viability after exposure to Aβ40 for 24 hrs was measured using a colorimetric XTT assay (Cell Proliferation Kit II, Roche, Mannheim, Germany) The release of lactate dehydrogenase (LDH) from the cytosol into the media was used to report the integrity of the cell membrane (Cytotoxicity Detection Kit-LDH, Roche, Mannheim, Germany).

Figure 9A:
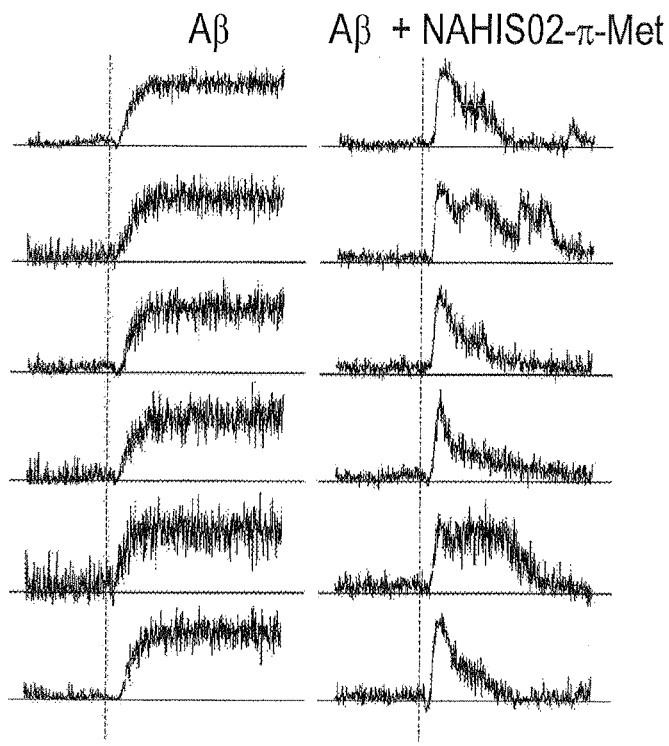
FIG. 9 illustrates the time course of the intracellular free calcium change in 6 selected fura-2AM loaded PC12 cells before and after the addition of either Aβ (7.66 µM) and Aβ+NAHIS02 (Panel A) or Aβ+NAHIS02-π-Met (Panel B).
Figure 9B:
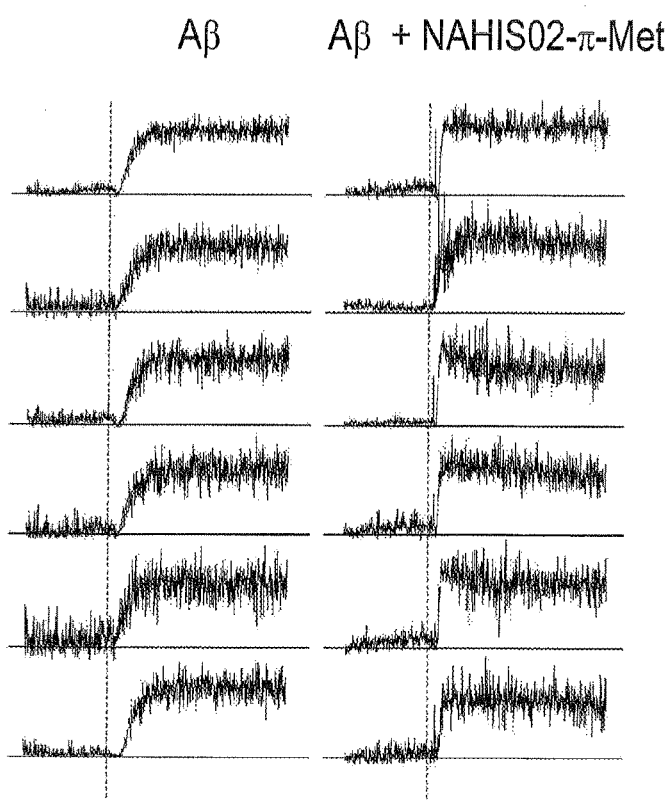

To determine if the imidazole groups of the histidine residues were responsible for the ability of the His-related compounds to protect cells against Aβ cytotoxicity, intracellular free calcium measurements were taken before and after the addition of either NAHIS02 (unmethylated imidazole groups) or NAHIS02-(π-Met) (methylated imidazole groups). A 15 minute time course experiment was performed of the intracellular free calcium change in six FURA-2AM loaded PC 12 cells before and after the addition of Aβ (7.66 µM) and Aβ+His-related compound (16.66 µM). FIG. 9 shows that the compound NAHIS02 has the capacity to block Aβ-induced intracellular calcium increase (Panel A) whereas NAHIS02-(π-Met) has lost this ability. Therefore, this result suggests that the ability of the His-related compounds to protect cells against Aβ cytotoxicity is due to the imidazole groups in the histidine residues.

Figure 10:
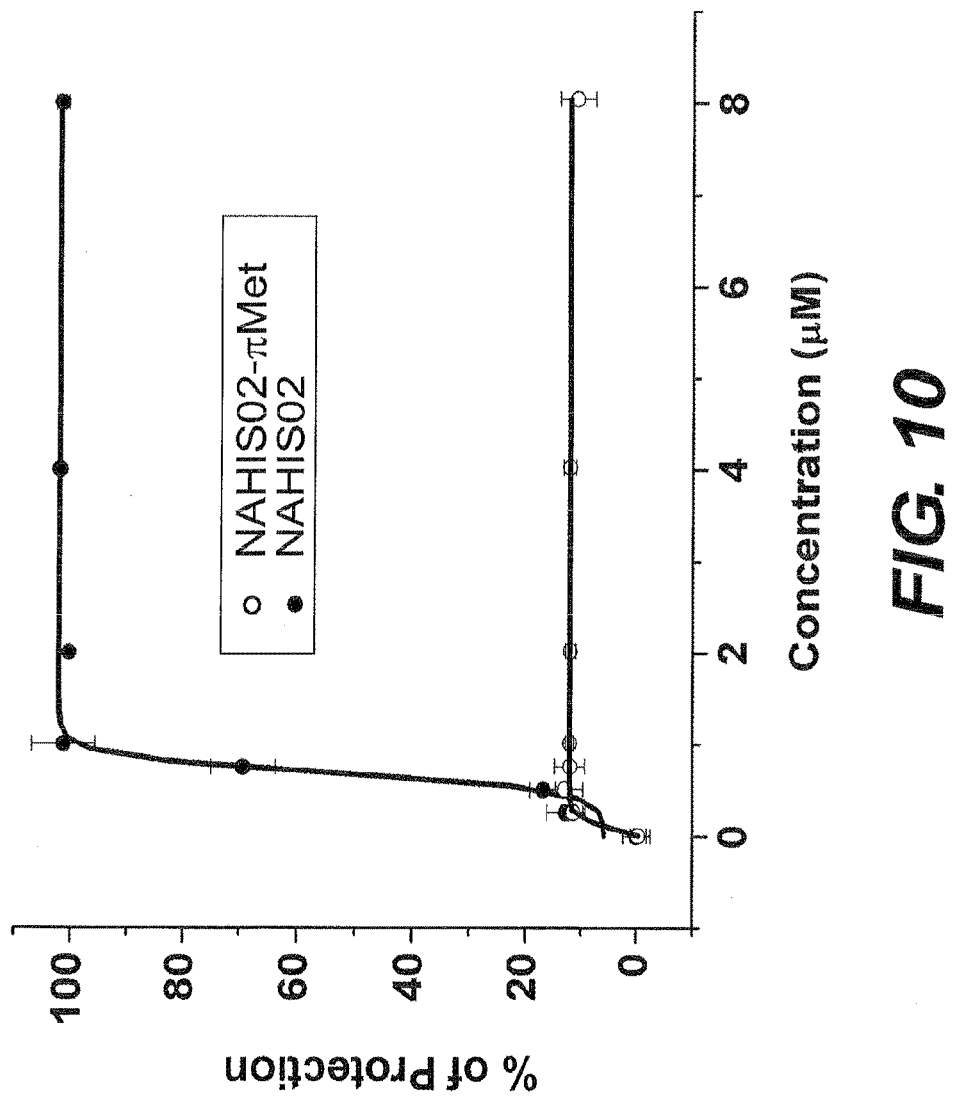
FIG. 10 shows the protection of PC12 cells from Aβ cytotoxicity after the addition of either NAHIS02 or NAHIS02-π-Met. INSERT PANEL INFO A-F

To further support these results, cell viability was determined in the presence of either NAHIS02 or NAHIS02-(π-Met) using the LDH assay to evaluate cell membrane integrity. FIG. 10 shows that NAHIS02-(π-Met) did not protect the cells against Aβ as seen for NAHIS02.

Example 7

Concentration Dependence Blockage of the Aβ-Induced Intracellular Calcium Response by the Aβ Channel Blocker NAHIS04

Experiments in this Example were performed to determine if there was concentration dependence blockage of the Aβ-induced intracellular calcium response by NAHIS04. A time course of the intracellular free calcium change was taken in FURA-2AM loaded PC12 cells before and after the addition of Aβ (7.66 µM) to media containing different concentrations of NAHIS04. FIG. 11 illustrates that the concentration of the Aβ channel blocker is important and that the most efficient concentration of NAHIS04 for the blockage occurred at >5 µM.

Example 8

Proposed Mechanism for Aβ Ion Channels Blockage by His-Related Compounds

The channel-like annular structure of Aβ oligomers, as has been observed by electron microscopy (Lashuel et al., 2002) and by atomic force microscopy (AFM) (Quist et al., 2005; Lal et al, 2007) suggests that to form an Aβ channel, Aβ subunits assemble in a polymeric transmembrane structure. Based on this structure, a series of theoretical models have been designed to shape the different forms that oligomers of Aβ assemble to form ion channels when incorporated into a lipid membrane (Durrell et al., 1994; Jang et al., 2007; Jang et al., 2008). The most recently developed models, which illustrate the atomistic structure of the Aβ channel in annular topology, followed molecular-dynamics simulations based on nuclear magnetic resonance data of the oligomers and use the universal U-shaped (strand-turn-strand) motif for the truncated $Aβ^{17-42}$ (Jang et al, 2007; Jang et al., 2008). Although these models do not include the first 16 residues of the Aβ subunits, which contain the His residues, the negatively charged side chains of $Glu^{22}$ are arranged circularly in the pore, inducing a cationic ring by the binding of cations such as $Mg^{2+}$, $Ca^{2+}$, $K^-$ and $Zn^{2+}$ (Jang et al., 2007; Jang et al., 2008). Former models were developed based on least-energy calculations, and assume that the channels are formed from an assembly of Aβ subunits arranged symmetrically around the axis of a pore lined by an amphipathic array of alternated charged residues. In this case the resulting models present rings of $His^{13}$ and $His^{14}$ residues of the Aβ molecule around the entrance of the putative pore (Durrell et al., 1994). If not all the His are protonated, this annular arrangement will model pores with a net negative charge to explain the cation selectivity of the Aβ channels. The theoretical models for the truncated $Aβ^{17-42}$ include the charged residues $Glu^{22}$ and $Lys^{28}$ of the Aβ subunit. The old model on energetic grounds for the full length $Aβ^{1-40}$ includes in addition the charged residues $His^6$, $His^{13}$ and $His^{14}$. Although the molecular-dynamics simulation successfully reproduce the channel dimensions, shapes and subunit organization of the Aβ channels observed with AFM (Quist et al., 2005; Lal et al., 2007), our results from using His-containing Aβ channel blockers could be better explained by a model that will represent the full length Aβ subunit. Such a model must include His residues in addition to the $Glu^{22}$ and $Lys^{28}$ charged residues. There are examples of the amino end of the Lys side chain and Glu acid side chain interacting with His residues. However, His prefers to interact in a face-to-face stacked orientation with His rings (Bhattacharyya et al., 2003; Saha et al., 2005). We speculate that this may provide stability to the assembly of Aβ subunits in a polymeric transmembrane channel structure. In this respect, disruption of this His-His interaction may prevent the functioning of Aβ channels. Recent experiments showed that perturbing the hydrogen bonding of the imidazole side chains of His residues of Aβ by selective methylation, prevents the formation of His bridges and results in abolition of the Aβ neurotoxicity (Tickler et al., 2005).

The addition of compounds of known His coordinating capacity such as $Ni^{2+}$ imidazole, His and a series of His-related compounds, to Aβ channel incorporated in membranes show that the His residues located in the N-terminal branch of the Aβ peptide sequence are essential to form the functional structure that constitute the selectivity filter and the ion pathway of the Aβ channel. To achieve the functional characteristic of the Aβ channels, the theoretical models, constructed to shape the different forms that oligomers of Aβ assemble to form ion channels, have to include the segment of the Aβ peptide that contains the charged His residues.

Figure 12A:
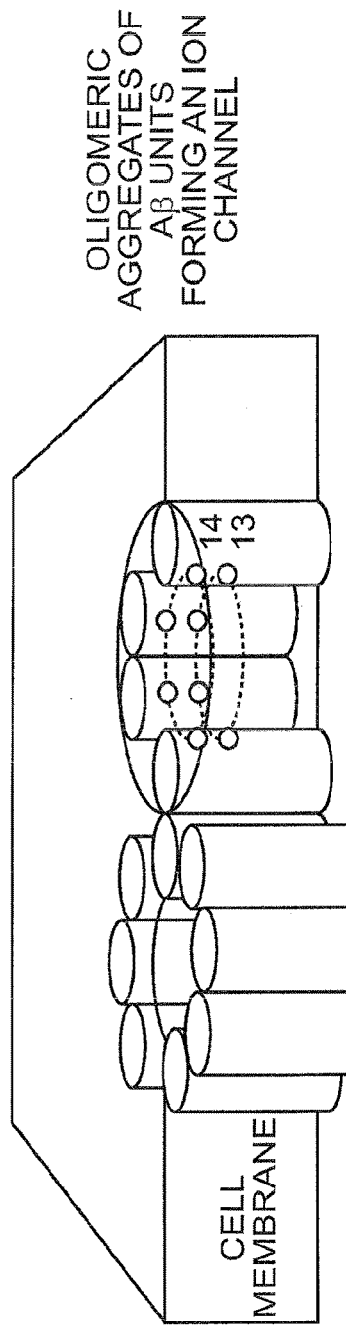
FIG. 12 illustrates a proposed mechanism for Aβ ion channels blockage by His-related compounds. Oligomeric aggregates of Aβ units forming an ion channel are shown in Panel A, one Aβ unit is shown in Panel B, and the blockage of the Aβ ion channel by His-related compounds is shown in Panel C.
Figure 12C:
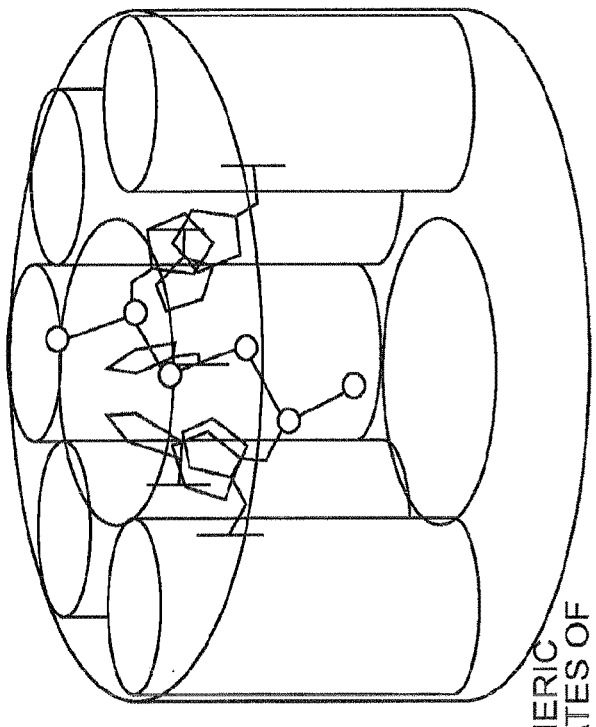
Figure 12B:
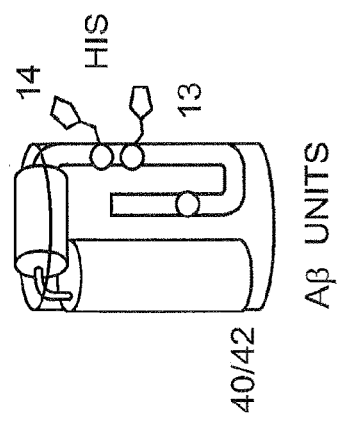

FIG. 12 depicts the proposed mechanism for the blockage of Aβ ion channels by the His-related compounds discussed herein. Panel A illustrates oligomeric aggregates of Aβ units forming an ion channel within the cell membrane. Panel B shows one Aβ unit with $His^{13}$ and $His^{14}$ labeled. Panel C depicts the blockage of the ion channel by the interactions between the imidazole groups from His or His-related compounds.

Example 9

Figure 13:
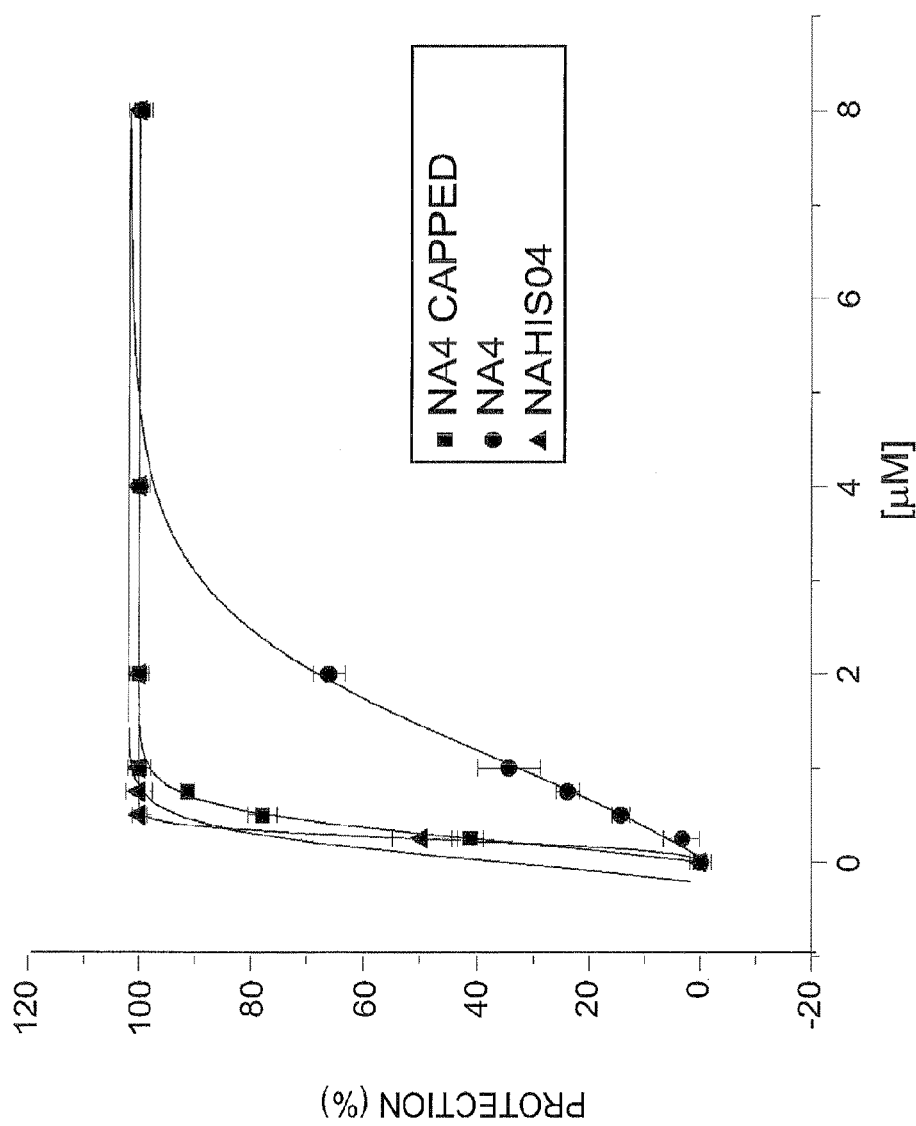
FIG. 13 shows the protection of PC12 cells from Aβ cytotoxicity after the addition of either NA4 capped (having an amidated carboxy terminus and an acetylated amino terminus), NA4 (with unmodified termini) or NAHIS04.

Capping the Free Carboxyl and Amine Ends of NA4 Improves its Efficacy in Blocking the Aβ Channel In Example 5, it was shown that NA4 was not as effective at blocking the Aβ channel as NAHIS04, which had modified carboxyl and amine ends of its His residues (FIG. 8). In this Example, NA4 was again compared to NAHIS04 as well as to a modified version of NA4, NA4mod, with end-capped His residues. As with other end-capped His residues, NA4mod had the carboxyl and amine groups of its His residues amidated and acetylated, respectively, leaving the imidazole side chains as the sole groups available for interaction with other reactive groups in the Aβ channel. As shown in FIG. 13 in a cell viability assay, capping the free carboxyl and amine ends of NA4 significantly improves its efficacy in blocking the Aβ channel. In fact, the percent protection is similar to the protection shown by NAHIS04, which also has end-capped His residues.

The results described in this investigation show that His-coordinating and His-related compounds can efficiently block Aβ channels incorporated into artificial membranes, and can also entirely prevent Aβ cytotoxicity produced by the incorporation of Aβ channels in the cell surface membrane. Therefore, we interpret these data to support the hypothesis that His residues within the Aβ channel sequence are in the pathway of ion flow and contribute to define the ion channel selectivity. Additionally, the data confirm the contribution of the Aβ channel to the cytotoxicity of Aβ.

The results of the investigation presented here indicate that Aβ channel blockage by compounds of known His-coordinating capacity such as $Ni^{2+}$ and imidazole, occurs by the interaction with the His residues located in the pathway of the ions in the Aβ channel. This conclusion is supported by the enhanced blocking efficiency observed after increasing the number of imidazole reactive side chains in His-related compounds. Additionally, we observed that perturbing the bonding of the imidazole side chains by selective methylation, which prevents the interplanar interaction of imidazole with the aromatic His residues, results in abolition of Aβ channel current activity and neurotoxicity.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

REFERENCES

The following references are cited in the application and provide general information on the field of the invention and provide assays and other details discussed in the application. The following references are incorporated herein for their disclosures, as they relate to the present invention.

Arispe N. J. 2004. Architecture of the Alzheimer's AβP ion channel. J. Memb. Biol. 197(1):33-48.

Arispe N, E. Rojas, and H. B. Pollard. 1993. Alzheimer disease amyloid β-protein forms calcium channels in bilayer membranes: blockade by tromethamine and aluminum. Proc. Natl. Acad. Sci. USA 90:567-571.

Arispe N, H. B. Pollard, and E. Rojas. 1994. The ability of Amyloid β-protein [AβP(1-40)] to form $Ca^{2+}$ channels provides a mechanism for neuronal death in Alzheimer's disease. Ann. New York Acad. Sc. 747: 256-266.

Arispe N., H. B. Pollard, and E. Rojas. 1996. $Zn^{2+}$ interaction with Alzheimer amyloid β protein calcium channels. Proc. Natl. Acad. Sci. 93:1710-1715.

Arispe, N., J. Diaz, and O. Simakova. 2007. Aβ ion channels. Prospects for treating Alzheimer's disease with Aβ channel blockers. Biochim. Biophys. Acta. 1768:1952-1965.

Becker A. B., and R. A. Roth. 1993. Identification of glutamate-169 as the third zinc-binding residue in proteinase III, a member of the family of insulin-degrading enzymes. Biochem J. 292 (Pt 1):137-142.

Bhattacharyya R, R. P. Saha, U. Samanta, and P. Chakrabarti. 2003. Geometry of Interaction of the Histidine Ring and other planar basic residues. J. Proteome Res. 2: 255-263.

Chakrabarti P. 1990. Geometry of interaction of metal ions with histidine residues in protein structures. Protein Eng. 4(1):57-63.

Chakrabarti P and R. Bhattacharyya. 2007. Geometry of non-bonded interactions involving planar groups in proteins. Progr. Biophys and Mol. Biol. 95:83-137.

Demuro A., E. Mina, R. Kayed, S. C. Milton, I. Parker, and C. G. Glabe. 2005. Calcium dysregulation and membrane disruption as a ubiquitous neurotoxic mechanism of soluble amyloid oligomers. J. Memb. Biol. 280(17):17294-300.

Diaz, J. C., J Linnehan, H. Pollard, and N. Arispe. 2006. Histidines 13 and 14 in the Aβ sequence are targets for inhibition of Alzheimer's disease Aβ ion channel and cytotoxicity. Biol. Res. 39:447-460.

Durrell S. R., H. R. Guy, N. Arispe, E. Rojas, and H. B. Pollard. 1994. Theoretical models of the ion channel structure of amyloid-β-protein. Biophys. J. 67:2137-2145.

Gilman A. G., T. W. Rall, A. S. Miles, and P. Taylor. 1993 The Pharmacological Basis of Therapeutics (8th ed), McGraw Hill, Inc., New York.).

Haass C. and Selkoe, D. J. 1993. Cellular processing of b-amyloid precursor peptide and the genesis of amyloid beta-peptide. Cell 75(6):1039-42.

Hardy, J. A., and G A Higgins. 1992. Alzheimer's disease: the amyloid cascade hypothesis. Science 256(5054):184-185.

Hardy, J. A., and D. J. Selkoe. 2002. The amyloid hypothesis of Alzheimer's disease: progress and problems on the road to therapeutics. Science 297(5580):353-356.

Jang H., J. Zheng, and R. Nussinov. 2007. Models of β-amyloid ion channels in the membrane suggest that channel formation in the bilayer is a dynamic process. Biophys. J. 93:1938-1949.

Jang H., J. Zheng, R. Lal and R. Nussinov. 2008. New structures help the modeling of toxic amyloidβ ion channels. Trends Biochem Sci. 33(2):91-100.

Kagan B. L., Y. Hirakura, R. Azimov, R. Azimova, and M.-C. Lin. 2002. The channel hypothesis of Alzheimer's disease: current status. Peptides 23:1311-1315.

Kawahara M. 2004. Disruption of calcium homeostasis in the pathogenesis of Alzheimer's disease and other conformational diseases. Current Alzheimer Res. 1:87-95.

Kawahara M., N. Arispe, Y. Kuroda, E. Rojas. 1997. Alzheimer's disease amyloid β-protein forms $Zn^{2+}$-sensitive cation-selective channels across excited membrane patches from hypothalamic neurons. Biophysical J. 73:67-75.

Kawahara M., Y. Kuroda, N. Arispe, and E. Rojas. 2000. Alzheimer's beta-amyloid, human islet amylin, and prion protein fragment evoke intracellular free calcium elevations by a common mechanism in a hypothalamic GnRH neuronal cell line. J. Biol. Chem. 275(19):14077-14083.

Kourie J. I., C. L. Henry, and P. Family. 2001. Diversity of amyloid beta protein fragment [1-40]-formed channels. Cell Mol Neurobiol. 3:255-84.

LaFerla F. M. 2002. Calcium dyshomeostasis and intracellular signaling in Alzheimer's disease. Nat. Rev. Neurosci. 3:862-872.

Lal R, H. Lin, and A. P. Quist. 2007. Amyloid beta ion channel: 3D structure and relevance to amyloid channel paradigm. Biochim Biophys Acta. 1768(8):1966-1975.

Lashuel H. A., D. Hartley, B. M. Petre, T. Wall, and P. T. Lansbury Jr. 2002. Neurodegenerative disease: amyloid pores from pathogenic mutations. Nature. 418(6895):291.

Lin H. Y. J. Zhu, and R. Lal. 1999. Amyloid b-protein (1-40) forms calcium-permeable $Zn^{2+}$ sensitive channels in reconstituted lipid vesicles. Biochemistry 38: 11189-11196.

Loo D. T., A. Copani, C. J. Pike, R. E. Whittemore, A. J. Walencewicz, and C. W. Cotman. (1993). Apoptosis is induced by β-amyloid in cultured central nervous system neurons. Proc. Natl. Acad. Sci. U.S.A. 90:7951-7955.

Mattson, M. P., B. Cheng, D. Davis, K. Bryant, I. Liberberg, and R. E. Rydel. 1992. β-Amyloid peptides destabilize calcium homeostasis and render human cortical neurons vulnerable to exicitoxicity. J. Neurosci. 12:376-389.

Mattson M. P., S. W. Barger, B. Cheng, I. Lieberburg, V. L. Smith-Swintosky, and R. E. Rydel. 1993. β-amyloid precursor protein metabolites and loss of neuronal calcium homeostasis in Alzheimer's disease. Trends Neurosci. 16:409-415.

Micelli D., V. Meleleo, E. Picciarelli, and E. Gallucci. 2004. Effects of sterols on β-amyloid peptide (AβP 1-40) channel formation and their properties in planar lipid membranes. Biophys. J. 86:2231-2237.

Miura T, K. Suzuki, N. Kohata, and H. Takeuchi. 2000. Metal binding modes of Alzheimer's amyloid beta-peptide in insoluble aggregates and soluble complexes. Biochemistry. 39(23):7024-31.

Mukherjee A. and B. Bagchi. 2006. Anomalous orientation-dependent effective pair interaction among histidine and other amino acid residues in metalloproteins: breakdown of the hydropathy scale index. Biochemistry 45:5129-5139.

Perlman R. K., and M. R. Rosner. 1994. Identification of zinc ligands of the insulin-degrading enzyme. J Biol Chem. 269(52):33140-33145.

Quist A., I. Doudevski, H. Lin, R. Azimova, D. Ng, B. Frangione, B. Kagan, J. Ghiso, and R. Lal. 2005. Amyloid ion channels: a common structural link for protein-misfolding disease. Proc. Natl. Acad. Sci. USA. 102(30):10427-10432.

Rhee S. K., A. P. Quist, and R. Lal. 1998. Amyloid β-protein (1-42) forms calcium-permeable-$Zn^{2+}$ sensitive channels. J. Biol. Chem 273:13379-13382.

Saha R. P., R. P. Bahadur, and P. Chakrabarti. 2005. Interresidue contacts in proteins and protein-protein interfaces and their use in characterizing the homodimeric interface. J. Proteome Res. 4:1600-1609.

Scheiner S, T. Kar, and J. Pattanayak. 2002. Comparison of various types of hydrogen bonds involving aromatic amino acids. J. Am. Chem. Soc. 124:13257-13264.

Simakova O., and N. Arispe. 2006. Early and late cytotoxic effects of external application of the alzheimer's Aβ result from the initial formation and function of ion channels. Biochemistry 45: 5907-5915.

Smith I. F., K. N. Green, and F. M. LaFerla. 2005. Calcium dysregulation in Alzheimer's disease: Recent advances gained from genetically modified animals. Cell Calcium 38:427-437.

Tickler A. K., D. G. Smith, G. D. Ciccotosto, D. J. Tew, C. C. Curtain, D. Carrington, C. L. Masters, A. I. Bush, R. A. Cherny, R. Cappai, J. D. Wade, and K. J. Barnham. 2005. Methylation of the imidazole side chains of the Alzheimer disease amyloid-beta peptide results in abolition of superoxide dismutase-like structures and inhibition of neurotoxicity. J Biol Chem. 280(14):13355-13363.

Yang D. S., J. McLaurin, K. Qin, D. Westaway, and P. E. Fraser. 2000. Examining the zinc binding site of the amyloid-beta peptide. Eur J. Biochem. 267(22):6692-6698.

Yankner, B. A. 1996. Mechanism of neuronal degeneration in Alzheimer's disease. Review. Neuron 16:921-932.

Yankner, B. A. 2000. The pathogenesis of Alzheimer's disease. Is amyloid beta-protein the beginning or the end?. Ann N Y Acad Sci. 924:26-28.

Zhu Y. J., H. Lin, and R. Lal. 2000. Fresh and nonfibrillar amyloid β protein(1-40) induces rapid cellular degeneration in aged human fibroblasts: evidence for AβP-channel-mediated cellular toxicity. FASEB J. 14(9):1244-1254.

| SEQUENCE LISTING |
|---|
| SEQ ID NO: 1 |
| DAEFRHDSGYEVHHQKLVFFAEDVGSNKGAIIGLMVGGVVIA |
| SEQ ID NO: 2 |
| [NAHIS04] |
| Ac-HHHH-CONH$_2$ |
| SEQ ID NO: 3 |
| [NA4] |
| SGYEVHH |
| SEQ ID NO: 4 |
| [NA7] |
| EVHHQKL |
| SEQ ID NO: 5 |
| [NA4 modified] |
| Ac-SGYEVHH-CONH2 |

The invention claimed is:

1. A method of treating Alzheimer's Disease in a subject, the method comprising administering to the subject an amount of a composition sufficient to treat Alzheimer's disease in the subject, wherein the composition comprises a compound of the formula:

(SEQ ID NO: 2)

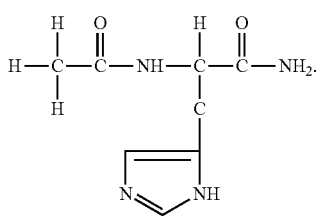 [SMILES: CC(=O)NC(Cc1cnc[nH]1)C(N)=O]

, or

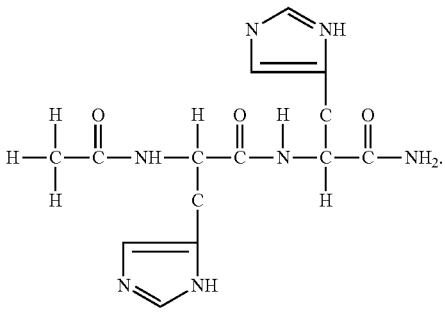

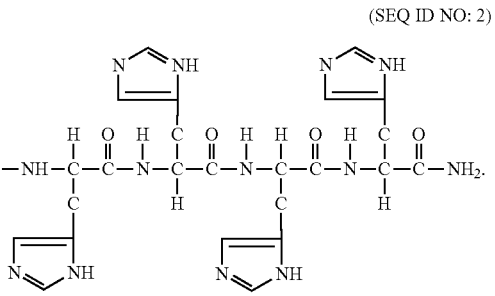

2. The method of claim 1, wherein the compound has the formula:

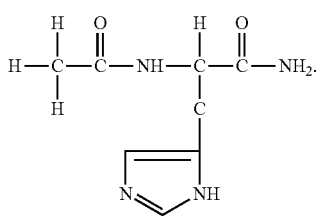 [SMILES: CC(=O)NC(Cc1cnc[nH]1)C(N)=O]

3. The method of claim 1, wherein the compound has the formula:

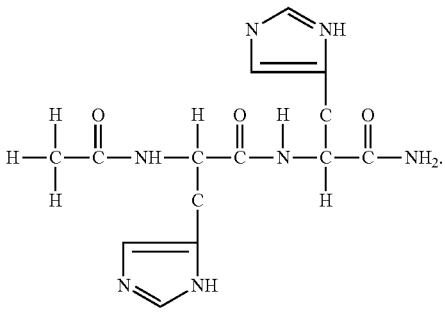

4. The method of claim 1, wherein the compound has the formula:

(SEQ ID NO: 2)

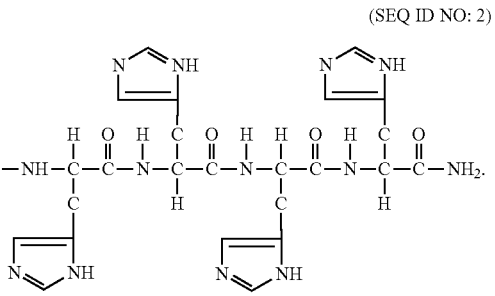

* * * * *